(12) United States Patent
Honma et al.

(10) Patent No.: US 7,399,644 B2
(45) Date of Patent: Jul. 15, 2008

(54) IMMUNOASSAY, REAGENT FOR IMMUNOASSAY, AND PRODUCTION METHOD OF THE SAME

(75) Inventors: Tsutomu Honma, Kanagawa (JP); Tetsuya Yano, Kanagawa (JP); Tsuyoshi Nomoto, Tokyo (JP); Shinya Kozaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 629 days.

(21) Appl. No.: 10/453,483

(22) Filed: Jun. 4, 2003

(65) Prior Publication Data

US 2004/0005638 A1 Jan. 8, 2004

(30) Foreign Application Priority Data

Jun. 13, 2002 (JP) .............................. 2002-173027
May 2, 2003 (JP) .............................. 2003-127099

(51) Int. Cl.
*G01N 33/551* (2006.01)
*G01N 33/532* (2006.01)
*G01N 33/543* (2006.01)
*G01N 33/569* (2006.01)
*G01N 33/573* (2006.01)
*C12Q 1/70* (2006.01)

(52) U.S. Cl. ............................. 436/524; 435/5; 435/7.1; 435/7.4; 435/69.3; 435/69.7; 435/176; 436/518; 436/523; 436/543; 436/547; 530/391.1; 530/391.9

(58) Field of Classification Search .................. 435/7.1, 435/7.4, 7.6, 176; 436/518, 523, 524, 528

See application file for complete search history.

(56) References Cited

U.S. PATENT DOCUMENTS

| | | | | |
|---|---|---|---|---|
| 4,373,932 A | * | 2/1983 | Gribnau et al. | ............. 436/501 |
| 5,489,537 A | | 2/1996 | Van Aken | .................. 436/534 |
| 5,561,045 A | * | 10/1996 | Dorval et al. | .................. 435/5 |
| 5,670,315 A | | 9/1997 | Yamamoto et al. | ............. 435/6 |
| 5,863,789 A | | 1/1999 | Komatsu et al. | ............. 435/262 |
| 5,981,296 A | | 11/1999 | Stout | ........................ 436/501 |
| 6,368,877 B1 | | 4/2002 | Zhang et al. | ................ 436/527 |
| 6,600,029 B1 | * | 7/2003 | Sherman et al. | ............ 536/23.2 |
| 6,951,745 B2 | * | 10/2005 | Nomoto et al. | ............. 435/118 |

FOREIGN PATENT DOCUMENTS

| | | |
|---|---|---|
| EP | 0 293 779 | 12/1988 |
| EP | 0 315 866 | 5/1989 |
| FR | 2 592 714 | 7/1987 |
| JP | 4-274762 | 9/1992 |
| JP | 11-295313 | 10/1999 |
| JP | 2000-338108 | 12/2000 |

OTHER PUBLICATIONS

"A Particle Agglutination Assay For Rapid Identification Of Heparin Binding To Coagulase-nagative *Staphylococci*," C. Pascu, et al., J. Med. Microbiol., vol. 45, pp. 263-269 (1996).
"A Review Of Factors Affecting The Performances Of Latex Agglutination Tests," J.L. Ortega-Vinuesa, et al., J. Biomater. Sci. Polymer Edn, vol. 12, No. 4, pp. 379-408 (2001).
Scott, Jamie K. & Smith, George P., "Searching for Peptide Ligands with an Epitope Library," 249 Science 386-90 (Jul. 1990).
Cwirla, Steven E. et al., "Peptides on Phage: A Vast Library of Peptides for Identifying Ligands," 87 Proc. Natl. Acad. Sci. USA 6378-82 (Aug. 1990).
Fodor, Stephen P.A. et al., "Light-Directed, Spatially Addressable Parallel Chemical Synthesis," 251 Science 767-73 (Feb. 1991).
Lam, Kit S. et al., "A New Type of Synthetic Peptide Library for Identifying Ligand-Binding Activity," 354 Nature 82-4 (Nov. 1991).
Houghten, Richard A. et al., "Generation and Use of Synthetic Peptide Combinatorial Libraries for Basic Research and Drug Discovery," 354 Nature 84-6 (Nov. 1991).
Chien, D.Y. et al. "Diagnosis of Hepatitis C Virus (HCV) Infection Using an Immunodominant Chimeric Polyprotein to Capture Circulating Antibodies: Reevaluation of the Role of HCV in Liver Disease," 89 Proc. Natl. Acad. Sci. USA 10011-15 (Nov. 1992).
"Seikagaku Jikken Ho 11 (Biochemical Experiment Method 11)," Enzyme Immunoassay, Tokyo Kagaku Dojin Co., Ltd., p. 270 (1989).

* cited by examiner

*Primary Examiner*—Long V. Le
*Assistant Examiner*—James L Grun
(74) *Attorney, Agent, or Firm*—Fitzpatrick, Cella, Harper & Scinto

(57) ABSTRACT

An assay method for determining presence of a target antibody or antigen in a specimen qualitatively or quantitatively by mixing the specimen with an antigen or antibody immunologically reactive with the target antibody or antigen, and assaying the level of the immunological agglutination reaction, wherein the reactive antigen or antibody is effectively immobilized on the carrier via an amino acid sequence capable of binding to the carrier.

1 Claim, No Drawings

IMMUNOASSAY, REAGENT FOR IMMUNOASSAY, AND PRODUCTION METHOD OF THE SAME

BACKGROUND OF THE INVENTION

1. Field of the Invention

The present invention relates to an immunoassay process of a target antibody or antigen in a specimen, which comprises mixing the specimen with an antigen or antibody corresponding to the target antibody or antigen to elicit immunoagglutination reaction, and then detecting or determining the agglutination state. The present invention also relates to a reagent used in the assay and a method for producing the reagent.

2. Related Background Art

In clinical laboratory tests, various components in biological samples such as blood or urine are assayed to diagnose various diseases, for which various assay methods have been developed and used. For example, enzymatic assays using enzyme reaction and immunoassays using antigen-antibody reaction have widely been used. In recent years, especially, immunoassay utilizing highly specific antigen-antibody reactions has been used more frequently because of its high accuracy.

In the field of environmental and food analysis, usually the target substances are extracted from the sample, concentrated and then analyzed by high performance liquid chromatography or gas chromatography. However, in recent years, as seen with problems of dioxin or endocrine disrupting chemicals (so-called environmental hormones), assay of substances of extremely low concentrations, assay of a wide variety of target species, rapid assay of a large number of specimens, etc. are required more and more, which conventional methods have difficulty to cope with. Thus, also in the field of environmental and food analysis, immunoassay using antigen-antibody reaction is beginning to be used.

Examples of immunoassay include immunoagglutination assay (immunonephelometry and latex agglutination assay), enzyme immunoassay, and radioimmunoassay, which may be selected to suit the purposes. Immunoagglutination assay, especially, are widely used as a simple on-site assay method, because it not necessarily requires large expensive assay apparatuses, and is capable of an easy determination by visual observation. In immunoagglutination assay, an antigen or an antibody is immobilized on a water-insoluble carrier, and the carrier is mixed with a specimen to elicit immune agglutination reaction, and the level of agglutination is determined. Generally, polystyrene latex or gelatin particles are used as the water-insoluble carrier particles (Japanese Patent Application Laid-Open Nos. 11-295313 and 2000-338108). Since these materials are white or transparent, so that special techniques and trainings are required to carry out visual determination.

In order to solve the above problem, use of a colored insoluble carrier such as a pigment or dye has been proposed for easy visual determination. Japanese Patent Application Laid-Open No. 4-274762 discloses an immunoagglutination assay that uses phthalocyanine pigment as an insoluble carrier to which antibody is immobilized by physical adsorption. As a result, the agglutinate formed by the immune agglutination reaction has a blue color, enabling easy visual determination of the reaction.

However, when an antigen or antibody is immobilized on an insoluble carrier such as pigment by physical adsorption, sufficient adsorption may not be attained at times, causing problems regarding the production efficiency and storage stability of the assay reagent. Moreover, when an antigen or antibody is immobilized by physical adsorption, due to the difference of hydrophobicity of antigen or antibody, constant and quantitative immobilization of antigen or antibody is often difficult. This seriously affects performance of the assay system, and causes difference between production lots.

To solve this problem, a method has been proposed in which an antibody is partially denatured to increase its hydrophobicity before the antibody is adsorbed onto an insoluble carrier (Seikagaku Jikken Ho 11 (Biochemical Experiment Method 11), Enzyme Immunoassay, Tokyo Kagaku Dojin Co., Ltd., p. 270, 1989). However, this method has a problem that the antibody may lose its activity by denaturation so that this method can be applied not to all types of antibody.

SUMMARY OF THE INVENTION

Thus, it is an object of the present invention to provide an improved immunoassay method to determine a target antibody or antigen in a specimen qualitatively or quantitatively. It is also an object of the present invention to provide a reagent used in the above assay and a method of producing the reagent.

The present inventors have found that peptides of certain amino acid sequences can bind to a carrier such as pigment by using screening a peptide library, and that when such peptides are fused to an antigen or an antibody by genetic engineering, the antigen or antibody can efficiently be immobilized on the surface of the carrier, thereby completed the present invention.

Thus, according to one aspect of the present invention, there is provided an assay method for determining a presence or an amount of a target antibody or antigen in a specimen comprising the steps of:

preparing a carrier on which an antigen or antibody corresponding to an antibody or antigen in said specimen respectively is immobilized;

mixing said carrier with said specimen; and assaying the level of an immunological agglutination reaction caused by said mixing step, wherein said antigen or antibody immobilized on said carrier is bound to said carrier via an amino acid sequence capable of binding to said carrier.

According to another aspect of the present invention, there is provided an assay reagent for assaying the presence or amount of a target antibody or antigen in a specimen, wherein an antigen or antibody corresponding to said antibody or antigen is immobilized on a carrier, and said antigen or antibody immobilized on said carrier is bound to said carrier via an amino acid sequence capable of binding to said carrier.

According to a further aspect of the present invention, there is provided a method of producing an assay reagent for assaying the presence or amount of a target antibody or antigen in a specimen, which comprises a step of immobilizing an antigen or antibody corresponding to said antibody or antigen on a carrier, wherein the antigen or antibody immobilized on said carrier is bound to said carrier via an amino acid sequence capable of binding to said carrier.

Herein, the term "to determine the presence or amount of an antibody or antigen" is used to assay the agglutinated state, that is, including both qualitative determination of the presence or absence of agglutination and quantitative determination of the agglutination level.

According to the present invention, an antigen or antibody can efficiently be immobilized on the surface of a carrier, and therefore the production process is extremely efficient.

Moreover, when a color material such as a pigment is used as a carrier, an assay reagent comprising an antigen or antibody immobilized on the surface of the color material has a certain color, so that it can be used as an assay reagent for clinical laboratory tests or environmental or food analysis, with easy visual determination and high reliability.

DETAILED DESCRIPTION OF THE PREFERRED EMBODIMENT

A carrier used in the present invention is not particularly limited, and any known carrier for an antigen or antibody used in the conventional antigen-antibody reaction can be used. Examples of such a carrier include organic polymer substances such as organic polymer latex obtained by emulsion polymerization of polystyrene, styrene-butadiene copolymer, styrene-methacrylic acid copolymer, polyglycidyl methacrylate, acrolein-ethylene glycol dimethacrylate copolymer, etc.; inorganic oxides such as silica, silica-alumina and alumina. Pigment can be also used as a carrier. Pigment usable as a carrier is not particularly limited. Examples of such pigment include black pigments such as carbon black, copper oxide, manganese dioxide, aniline black, activated carbon, nonmagnetic ferrite, and magnetite; yellow pigments such as chrome yellow, zinc yellow, yellow iron oxide, cadmium yellow, mineral fast yellow, nickel titanium yellow, Naples yellow, naphthol yellow S, hansa yellow G, hansa yellow 10G, benzidine yellow G, benzidine yellow GR, quinoline yellow lake, permanent yellow NCG, and tartrazine lake; orange pigments such as red chrome yellow, molybdenum orange, permanent orange GTR, pyrazolone orange, Vulcan orange, benzidine orange G, indanthrene brilliant orange RK, and indanthrene brilliant orange GK; red pigments such as iron oxide red, cadmium red lead, mercuric sulfide, cadmium, permanent red 4R, lithol red, pyrazolone red, watching red, calcium salt, lake red C, lake red D, brilliant carmine 6B, brilliant carmine 3B, eosin lake, rhodamine lake B, and alizarin lake; blue pigments such as iron blue, cobalt blue, alkali blue lake, Victoria blue lake, phthalocyanine blue, nonmetallic phthalocyanine blue, partially chlorinated phthalocyanine blues, fast sky blue, and indanthrene blue BC; violet pigments such as manganese violet, fast violet B, and methyl violet lake; green pigments such as chromium oxide, chrome green, pigment green B, malachite green lake, and final yellow green G; white pigments such as flowers of zinc, titanium oxide, antimony white, and zinc sulfide; extenders such as barite powder, barium carbonate, clay, silica, white carbon, talc, and alumina white; and other pigments. However, available pigments are not limited thereto.

In addition, the above described organic polymeric substance colored with a pigment or dye can be used as a carrier. In such a case, it is preferable to encapsulate the colorant in the polymer so that the colorant would not diffuse from the carrier.

The shape of the carrier can be selected appropriately depending on the purpose. For example, when an assay target is an antigen and the corresponding antibody is immobilized on the surface of a carrier, particles of 1 nm to 10 μm in diameter may be preferably used, more preferably, particles of 50 nm to 1 μm may be used.

In the present invention, the antigen or antibody corresponding to a target antibody or antigen (counter antigen or antibody) is not particularly limited. It may be a protein or peptide derived from an organism, a partially modified protein or peptide thereof, an artificially designed protein or peptide, or a fragment thereof, so long as it can cause an antigen-antibody reaction with the target antibody/antigen. For example, when a target is an antigen and the corresponding antibody is immobilized on the surface of a carrier, either a monoclonal antibody or polyclonal antibodies can be used. Alternatively, when a target is an antibody and the corresponding antigen is immobilized on the surface of a carrier, either a protein or peptide can be used as the above antigen.

For example, when presence of antibodies to Hepatitis C virus (HCV antibodies) in the blood is assayed to diagnose Hepatitis C virus (HCV) infection, known antigenic proteins of the Hepatitis C virus that can elicit antigen-antibody reaction with HCV antibodies can be used as the antigen. For example, one can use at least one selected from the group consisting of structure proteins such as HCV core proteins or envelope proteins, nonstructural proteins such as NS1 protein, NS2 protein, NS3 protein, NS4 protein and NS5 protein, and fragments thereof (Proc. Natl. Acad. Sci. USA, 89, 10011-10015, 1992). Alternatively, modified antigens having addition, deletion, substitution and/or insertion in the amino acid sequence of the above described antigen protein can also be used, as long as it has antigenicity sufficient to carry out the method of the present invention.

In order to obtain a peptide of an amino acid sequence capable of binding to the carrier (carrier-binding amino acid sequence) of the present invention, for example, the following phage display peptide library method can be used. A phage random peptide library may be constructed, for example, by ligating a synthetic gene of random sequence to a gene encoding a surface protein (e.g., gene III protein) of M13 phage to display the gene product fused to the N-terminus of the surface protein (Scott J K and Smith G P, Science, 249, 386, 1990, Cwirla S E et al., Proc. Natl. Acad. Sci. USA, 87, 6378, 1990). The size of the synthetic gene to be inserted is not particularly limited, as long as it enables stable peptide expression. However, in order that the prepared library may contain all of random sequences and displayed peptides may have binding ability, the gene length encoding 6 to 40 amino acids (which corresponds to a molecular weight of approximately 600 to 4,000) is suitable, more preferably 7 to 18 amino acids.

To select phages binding to a carrier of interest, the carrier is immobilized in a column or on a plate and contacted with the above library, and then non-binding phages are washed away by washing the column or plate while binding phages are retained. After washing, the retained phages are eluted with acid or the like, and they are then neutralized with a buffer. The neutralized phages are infected to *Escherichia coli* for amplification. This selection is repeated several times, so that clones capable of binding to a carrier of interest are condensed. To isolate a single clone, *E. coli* infected with these phages are grown on a culture plate to form single colonies. Each single colony is cultured in a liquid medium, and thereafter, phages existing in the supernatant of the medium are purified by precipitation with polyethylene glycol or the like. Analysis of the nucleotide sequence reveals the sequence of a binding peptide of interest. To prepare a peptide library having random amino acid sequences, not only the above phage method, but also a method of chemically synthesized peptides can be used. For example, beads method (Lam, K. S. et al., Nature, 354, 82, 1991), liquid phase focusing method (Houghton, R. A. et al., Nature, 354, 84, 1991), microplate method (Fodor, S. P. A. et al., Science, 251, 767, 1991), and other methods have been reported, and any of these methods can be applied in the present invention.

When two or more types of carrier-binding amino acid sequence are obtained by screening a phage display peptide library, all or part of these sequences may be ligated in suitable combination to use as a carrier-binding amino acid sequence. In this case, it is desired to place a suitable spacer sequence between two amino acid sequences. A preferred spacer sequence consists of three to approximately 400 amino acids. Further, such a spacer sequence may include any amino acid. Most importantly, spacers would not interfere the interaction between the assay target and an antigen or antibody, and not prevent binding of the antigen or antibody to the carrier.

Carrier-binding amino acid sequences of the present invention can be obtained not only by screening of a random peptide library but also by reasonably designing the sequence on the basis of the chemical properties of the carrier.

Such a carrier-binding amino acid sequence obtained by one of the above methods is used generally by fusing it to a counter antigen or antibody by genetic engineering. A carrier-binding amino acid sequence may be expressively fused to the N-terminus or C-terminus of a counter antigen or antibody. A suitable spacer sequence may be inserted between them.

A preferred spacer sequence is a sequence consisting of 3 to approximately 400 amino acids. Further, such a spacer may contain any amino acid. Most importantly, spacers would not interfere the interaction between the assay target and a counter antigen or antibody, and not prevent binding of the antigen or antibody to the carrier.

The fusion of a carrier-binding peptide and a counter antigen or antibody can be isolated and purified by any method, as long as the activity of the antigen or antibody can be maintained.

A step of immobilizing a counter antigen or antibody to a carrier can be achieved by contacting a fusion of a counter antigen or antibody and carrier-binding amino acid sequence with a carrier in an aqueous solvent.

The composition of an aqueous solvent is not particularly limited in this step, and various buffer solutions can be used. Preferably, buffers used in biochemistry can be used, such as acetate buffer, phosphate buffer, potassium phosphate buffer, 3-(N-morpholino)propanesulfonic acid (MOPS) buffer, N-tris(hydroxymethyl)methyl-3-aminopropanesulfonic acid (TAPS) buffer, tris HCl buffer, glycine buffer, or 2-(cyclohexylamino)ethanesulfonic acid (CHES) buffer. The buffer solution can be used in ordinary concentrations of 5 mM to 1.0 M, preferably, 10 to 200 mM. pH is controlled at 5.5 to 9.0, preferably at 7.0 to 8.5, but depending on conditions applied, pH is not limited to this range.

In order to retain the dispersed state of a carrier in an aqueous solvent, a suitable surfactant may be added, as long as the type and concentration of the additive surfactant do not hinder the subsequent steps. Examples of such a surfactant include anionic surfactants such as sodium oleate, sodium dodecylsulfonate, sodium dodecylsulfate, sodium N-dodecylsarcosinate, sodium cholate, sodium deoxycholate or sodium taurodeoxycholate; cationic surfactants such as cetyl trimethyl ammonium bromide or dodecyl pyridium chloride; ampholytic surfactants such as 3-[(chloamidopropyl)dimethyl-ammonio]-1-propanesulfonate (CHAPS), 3-[(3-chloamidopropyl)dimehyl-ammonio]-2-hydroxy-1-propanesulfonate (CHAPSO), palmitoyl lysolecithin or dodecyl-β-alanine; nonionic surfactants such as octyl glycoside, octyl thioglycoside, heptyl thioglycoside, decanoyl-N-methyl glucamide (MEGA-10), polyoxyethylene dodecyl ether (Brij, Lubrol), polyoxyethylene-i-octylphenyl ether (Triton X), polyoxyethylene nonylphenyl ether (Nonidet P-40, Triton N), polyoxyethylene fatty acid ester (Span) or polyoxyethylene sorbitol ester (Tween); and other surfactants.

Furthermore, in order to retain the dispersed state of a powdery carrier in an aqueous solvent, a suitable auxiliary solvent may be added, as long as the type and concentration of the additive auxiliary solvent do not hinder the subsequent steps. The auxiliary solvent can be selected from the group consisting of straight chain aliphatic hydrocarbons such as hexane, monohydric alcohols such as methanol or ethanol, polyhydric alcohols such as glycerol, fatty acid ethers, and carboxylic acid ethers, derivatives thereof, and combinations thereof.

As described above, the above fusion counter antigen or antibody is immobilized to a carrier by mixing the carrier with the fusion in a certain aqueous solvent at a certain concentration. In this case, a reactor is desirably shaken or stirred at a suitable strength so that the fusion antigen or antibody can bind uniformly to the surface of the carrier.

The immobilized amount can be determined by, for example, applying to a carrier a solution of a fused antigen or antibody of a known concentration for immobilization, and determining the protein concentration of the solution after immobilization reaction to calculate the immobilized amount by subtraction.

The immobilized antigen or antibody produced as described above can be used as it is, but it may be subjected to freeze-drying etc. before use.

Time of the immobilization treatment for an antigen or antibody is desirably 1 minute to 24 hours, and more desirably 10 minutes to 1 hour. Excessively long treatment is not preferable because the activity of the antigen or antibody may decrease.

In the present invention, additives such as an organic solvent, pigment, dye, indicator, surfactant, antiseptic, protective or inorganic salts may be used with the above components, according to necessity.

According to the present invention, an antigen or antibody can be immobilized efficiently on the surface of a carrier, and the production process is thereby extremely efficient.

When a color material such as a pigment is used as the carrier, the fusion antigen or antibody described above can be used as an assay reagent of high reliability for clinical laboratory tests, environmental and food analysis, because of easy visual determination as well as high quantitativity.

EXAMPLES

The present invention is further described in the following Examples. These Examples are provided only for illustrating embodiments of the present invention, and are not intended to limit the technical scope of the present invention.

Although a pigment was used as a carrier in the following Examples, the carrier is not limited thereto, but any known carrier of an antigen or antibody that is used in the conventional antigen-antibody reaction can be used with no particular limits.

Reference Example 1

Obtainment of Antigen Protein to Hepatitis C Virus Antibody

To 0.5 ml of human serum (Hepatitis B virus negative, GPT higher than 100 U), 2.5 ml of a guanidium thiocyanate solution (4 M guanidium thiocyanate, 10 mM EDTA, 0.1 M 2-mercaptomethanol, 2% sarcosyl, 50 mM Tris-HCl, pH 7.6) was added, and then total RNA in the serum was extracted by phenol/chloroform extraction, and purified by ethanol precipitation using glycogen as a carrier. Thereafter, cDNA was prepared from the obtained RNA using random hexamers as primers according to the method of Okamoto et al. (Japan J. Exp. Med., 60(3), 167-177, 1990) with a cDNA synthesis system (Boehringer Mannheim). Using this cDNA as a template, a DNA fragment of interest was amplified by PCR. The 5'-terminus of the amplified DNA was phosphorylated with T4 polynucleotide kinase, and then cloned by ligating it to plasmid pUC18 (Amersham Pharmacia Biotech) digested with a restriction enzyme SmaI. The HCV cDNA cloned into the plasmid was sequenced using Sequenase Sequence kit (United States Biochemical). From the obtained nucleotide sequence, a portion encoding an antigen protein NS4 of interest was selected. That portion was inserted into the SmaI-cleaved site of the plasmid pUC18 according to the conventional method so as to construct a plasmid pUC18-NS.

Example 1

Obtainment of Amino Acid Sequence Capable of Binding to Copper Phthalocyanine (1) Copper phthalocyanine (α form, Tokyo Kasei Kogyo Co., Ltd.) was suspended in a TBS buffer (50 mM Tris-HCl, pH 7.5, 150 mM NaCl) containing 0.1% Tween-20, at a concentration of 5 mg/ml. 10 µl of the suspension was put in an Eppendorf tube, and 990 µl of a TBST buffer (a TBS buffer+0.1% Tween-20) was further added thereto for dilution.

(2) Approximately $4 \times 10^{10}$ pfu of Ph. D. –12 phage display peptide library (New England BioLabs) was added to the tube, and was left to stand at 25° C. for 10 minutes.

(3) The tube was subjected to centrifugation (20,630×g, 5 minutes). Thereafter, the supernatant was discarded, and the pigment was recovered as a precipitate. The recovered pigment was suspended in a TBST buffer again, and washed 10 times by repeating centrifugation.

(4) 100 µl of an elution buffer (0.2 M Glycine-HCl, pH 2.2, 1 mg/ml BSA) was added thereto and the suspension was left to stand for 1 minute, and then centrifuged (20,630×g, 5 minutes). The obtained supernatant was transferred into another Eppendorf tube, to which 15 µl of 1 M Tris-HCl (pH 9.1) was added for neutralization. Thus the eluted phages were obtained.

(5) The eluted phages were used to infect E. coli ER2537 (New England BioLabs) cells in its early logarithmic growth phase were infected to be amplified therein. Culture was carried out at 37° C. for 4.5 hours. Thereafter, the amplified phages were separated from the cells by centrifugation, and then purified by precipitation with polyethylene glycol. The thus amplified and purified phages were then suspended in a TBS buffer, and the titer was determined by using an appropriate dilution series to infect E. coli cells.

(6) The above steps (1) to (5) were repeated three times using amplified phages. However, the concentration of Tween-20 in the TBS buffer was increased to 0.5% to establish more strict washing conditions.

From the second cycle, the same operations were carried out using an Eppendorf tube not containing pigment as a control. The titer of the eluted phages in each cycle is shown in Table 1.

TABLE 1

Titer of phage eluted in each cycle

| | Stock solution (A) | Binding to control (B) | Binding to phthalocyanine (C) | C/A | C/B |
|---|---|---|---|---|---|
| 1st cycle | $4.0 \times 10^{11}$ | | $1.2 \times 10^{6}$ | $3.0 \times 10^{-6}$ | |
| 2nd cycle | $1.6 \times 10^{11}$ | $1.1 \times 10^{5}$ | $1.7 \times 10^{5}$ | $1.1 \times 10^{-5}$ | 1 |
| 3rd cycle | $2.0 \times 10^{11}$ | $1.6 \times 10^{5}$ | $3.0 \times 10^{8}$ | $1.5 \times 10^{-3}$ | 1800 |
| 4th cycle | $1.7 \times 10^{11}$ | $2.7 \times 10^{6}$ | $5.3 \times 10^{9}$ | $3.1 \times 10^{-2}$ | 2000 |

(Units of A, B and C: pfu/ml)

For cloning of the finally eluted phages, excessive E. coli cells were infected with the phages. ssDNA was then prepared from each clone amplified in E. coli. Thereafter, the random region was sequenced to determine the amino acid sequence of the displayed peptide, whereby the amino acid sequence capable of binding to copper phthalocyanine was determined for each clone. The determined amino acid sequences and their frequencies are shown in Table 2.

TABLE 2

Determined amino acid sequences and their frequencies

| Determined amino acid sequences | Numbers (A) | Frequencies (A/36) |
|---|---|---|
| Lys-Tyr-Asp-Ser-Arg-His-Leu-His-Thr-His-Ser-His (SEQ ID NO 1) | 6 | 0.17 |
| Pro-Asn-Arg-Leu-Gly-Arg-Arg-Pro-Val-Arg-Trp-Glu (SEQ ID NO 2) | 6 | 0.17 |
| Lys-Cys-Cys-Tyr-Tyr-Asp-His-Ser-His-Ala-Leu-Ser (SEQ ID NO 3) | 4 | 0.11 |
| Glu-Tyr-Leu-Ser-Ala-Ile-Val-Ala-Gly-Pro-Trp-Pro (SEQ ID NO 4) | 3 | 0.08 |
| Lys-Leu-Trp-Ile-Leu-Glu-Pro-Thr-Val-Thr-Pro-Thr (SEQ ID NO 5) | 3 | 0.08 |
| Gln-Ser-Asn-Leu-Lys-Val-Ile-Pro-Ser-Trp-Trp-Phe (SEQ ID NO 6) | 3 | 0.08 |
| Trp-Ile-Pro-Pro-Gln-Trp-Ser-Arg-Leu-Ile-Glu-Pro (SEQ ID NO 7) | 3 | 0.08 |
| Asp-His-Pro-Gln-Ala-Lys-Pro-Asn-Trp-Tyr-Gly-Val (SEQ ID NO 8) | 1 | 0.02 |
| Gly-Leu-Pro-Pro-Tyr-Ser-Pro-His-Arg-Leu-Ala-Gln (SEQ ID NO 9) | 1 | 0.02 |
| Lys-Leu-Thr-Thr-Gln-Tyr-Met-Ala-Arg-Ser-Ser-Ser (SEQ ID NO 10) | 1 | 0.02 |
| Lys-Val-Trp-Met-Leu-Pro-Pro-Leu-Pro-Gln-Ala-Thr (SEQ ID NO 11) | 1 | 0.02 |
| Asn-Val-Thr-Ser-Thr-Ala-Phe-Ile-Asp-Thr-Pro-Trp (SEQ ID NO 12) | 1 | 0.02 |
| Arg-Leu-Asn-Leu-Asp-Ile-Ile-Ala-Val-Thr-Ser-Val (SEQ ID NO 13) | 1 | 0.02 |
| Thr-Leu-Pro-Ser-Pro-Leu-Ala-Leu-Leu-Thr-Val-His (SEQ ID NO 14) | 1 | 0.02 |
| Thr-Asn-Arg-His-Asn-Pro-His-His-Leu-His-His-Val (SEQ ID NO 15) | 1 | 0.02 |

Example 2

Obtainment of Amino Acid Sequence Capable of Binding to Carbon Black (1) Carbon black (Sigma-Aldrich Japan, K.K.) was suspended in a TBS buffer (50 mM Tris-HCl with pH 7.5, 150 mM NaCl) containing 0.1% Tween-20 to a concentration of 5 mg/ml. 10 µl of the suspension was put in an Eppendorf tube, and 990 µl of a TBST buffer (a TBS buffer+0.1% Tween-20) was further added thereto for dilution.

(2) Approximately $4 \times 10^{10}$ pfu of Ph. D. -12 phage display peptide library (New England BioLabs) was added to the tube, and was left to stand at 25° C. for 10 minutes.

(3) The tube was subjected to centrifugation (20,630×g, 5 minutes). Thereafter, the supernatant was discarded, and the pigment was recovered as a precipitate. The recovered pigment was suspended in a TBST buffer again, and washed 10 times by repeating centrifugation.

(4) 100 µl of an elution buffer (0.2 M Glycine-HCl, pH 2.2, 1 mg/ml BSA) was added thereto and left to stand for 1 minute, and then centrifuged (20,630×g, 5 minutes). The obtained supernatant was transferred into another Eppendorf tube, to which 15 µl of 1 M Tris-HCl (pH 9.1) was added for neutralization. Thus the eluted phages were obtained.

(5) The eluted phages were used to infect *E. coli* ER2537 (New England BioLabs) cells in its early logarithmic growth phase were infected to be amplified therein. Culture was carried out at 37° C. for 4.5 hours. Thereafter, the amplified phages were separated from the cells by centrifugation, and then purified by precipitation with polyethylene glycol. The thus amplified and purified phages were then suspended in a TBS buffer, and the titer was determined by using an appropriate dilution series and *E. coli* cells.

(6) The above steps (1) to (5) were repeated four times using amplified phages. However, the concentration of Tween-20 in the TBS buffer was increased to 0.5% to establish more strict washing conditions.

From the second cycle, the same operations were carried out using an Eppendorf tube not containing pigment as a control. The titer of the eluted phages in each cycle is shown in Table 3.

The titer of the eluted phage in each cycle is shown in Table 3.

TABLE 3

Titer of phage eluted in each cycle

| | Stock solution (A) | Binding to control (B) | Binding to carbon black (C) | C/A | C/B |
|---|---|---|---|---|---|
| 1st cycle | $4.0 \times 10^{11}$ | | $8.9 \times 10^{6}$ | $2.2 \times 10^{-5}$ | |
| 2nd cycle | $1.6 \times 10^{11}$ | $1.1 \times 10^{5}$ | $3.8 \times 10^{6}$ | $2.4 \times 10^{-5}$ | 35 |
| 3rd cycle | $2.0 \times 10^{11}$ | $1.6 \times 10^{5}$ | $6.0 \times 10^{6}$ | $3.0 \times 10^{-5}$ | 40 |
| 4th cycle | $1.7 \times 10^{11}$ | $1.1 \times 10^{6}$ | $1.5 \times 10^{8}$ | $8.8 \times 10^{-4}$ | 140 |
| 5th cycle | $1.9 \times 10^{11}$ | $2.0 \times 10^{6}$ | $2.7 \times 10^{9}$ | $1.4 \times 10^{-2}$ | 1400 |

(Units of A, B and C: pfu/ml)

For cloning of the finally eluted phages, excessive *E. coli* cells were infected with the phages. ssDNA was then prepared from each clone amplified in *E. coli*. Thereafter, the random region was sequenced to determine the amino acid sequence of the displayed peptide, whereby the amino acid sequence capable of binding to carbon black was determined for each clone. The obtained amino acid sequences and their frequencies are shown in Table 4.

TABLE 4

Determined amino acid sequences and their frequencies

| Determined amino acid sequences | Numbers (2) | Frequencies (A/38) |
|---|---|---|
| Trp-Pro-His-Ala-Trp-Lys-Val-Trp-Trp-Pro-Ala-Ser (SEQ ID NO 16) | 4 | 0.10 |
| Asn-Trp-Trp-Trp-Pro-Pro-Tyr-Ile-Arg-His-Gln-Pro (SEQ ID NO 17) | 3 | 0.08 |
| Trp-His-Trp-Ser-Trp-Thr-Pro-Trp-Pro-Ser-His-His (SEQ ID NO 18) | 2 | 0.05 |
| Trp-Pro-Trp-Ala-Trp-His-Pro-Ser-Arg-Asp-Val-Tyr (SEQ ID NO 19) | 2 | 0.05 |
| Trp-His-Gly-Tyr-Trp-Tyr-Ser-Asn-Leu-Asn-Thr-Thr (SEQ ID NO 20) | 2 | 0.05 |
| Trp-Trp-Thr-Pro-Trp-Met-Ser-His-Arg-Tyr-Pro-Val (SEQ ID NO 21) | 2 | 0.05 |
| Trp-Pro-Asn-Pro-Tyr-Trp-Gly-Trp-Phe-Ala-Ala-Val (SEQ ID NO 22) | 2 | 0.05 |
| Thr-Ser-Trp-His-Thr-Trp-Trp-Trp-Arg-Gln-Pro-Pro (SEQ ID NO 23) | 2 | 0.05 |
| Asn-Ala-Trp-His-Lys-Tyr-Trp-Trp-Pro-Ile-Thr-Lys (SEQ ID NO 24) | 2 | 0.05 |
| His-Pro-Asn-Asn-Asp-Trp-Ser-Lys-Ala-Pro-Gln-Phe (SEQ ID NO 25) | 2 | 0.05 |
| Trp-Trp-Thr-Pro-Gln-Pro-Trp-Trp-Ser-Phe-Pro-Ile (SEQ ID NO 26) | 1 | 0.03 |
| Trp-Pro-His-Thr-Ser-Trp-Trp-Gln-Thr-Pro-Leu-Thr (SEQ ID NO 27) | 1 | 0.03 |
| Trp-His-Val-Asn-Trp-Asp-Pro-Met-Ala-Trp-Tyr-Arg (SEQ ID NO 28) | 1 | 0.03 |
| Ser-Trp-Pro-Trp-Trp-Thr-Ala-Tyr-Arg-Val-His-Ser (SEQ ID NO 29) | 1 | 0.03 |
| Trp-His-Ser-Asn-Trp-Tyr-Gln-Ser-Ile-Pro-Gln-Val (SEQ ID NO 30) | 1 | 0.03 |
| Gly-Tyr-Trp-Pro-Trp-Lys-Phe-Glu-His-Ala-Thr-Val (SEQ ID NO 31) | 1 | 0.03 |
| Ala-Trp-Trp-Pro-Thr-Thr-Phe-Pro-Pro-Tyr-Tyr-Tyr (SEQ ID NO 32) | 1 | 0.03 |

TABLE 4-continued

Determined amino acid sequences and their frequencies

| Determined amino acid sequences | Numbers (2) | Frequencies (A/38) |
|---|---|---|
| Asn-Pro-Trp-Trp-Ser-His-Tyr-Tyr-Pro-Arg-Ser-Val (SEQ ID NO 33) | 1 | 0.03 |
| Trp-Pro-His-Asn-Tyr-Pro-Leu-Asn-His-Ser-Asn-Pro (SEQ ID NO 34) | 1 | 0.03 |
| Thr-Trp-Ala-His-Pro-Leu-Glu-Ser-Asp-Tyr-Leu-Arg (SEQ ID NO 35) | 1 | 0.03 |
| His-Thr-Tyr-Tyr-His-Asp-Gly-Trp-Arg-Leu-Ala-Pro (SEQ ID NO 36) | 1 | 0.03 |
| Thr-Phe-Val-Gln-Thr-Pro-Leu-Ser-His-Leu-Ile-Ala (SEQ ID NO 37) | 1 | 0.03 |
| Arg-Val-Pro-Pro-Ser-Lys-Leu-Thr-Arg-Pro-Pro-Phe (SEQ ID NO 38) | 1 | 0.03 |
| His-Ser-Ile-Tyr-Ser-Val-Thr-Pro-Ser-Thr-Ala-Ser (SEQ ID NO 39) | 1 | 0.03 |
| Leu-Asn-Thr-Gln-Asn-His-Ala-Pro-Leu-Pro-Ser-Ile (SEQ ID NO 40) | 1 | 0.03 |

Example 3

Production of Antigen Protein Capable of Binding to Copper Phthalocyanine

With an upstream primer (5'-TTCACAGGATCCACTGAGCTCGATGCC CAC-3') and an downstream primer (5'-GATCTGGGCTCGAGCCGACTAGTA GTCGCT-3') for a nucleotide sequence encoding the antigen protein NS4, PCR was carried out using the plasmid pUC18-NS prepared in Reference Example as a template. The obtained DNA fragment had BamHI/SacI restriction site in the upstream region and SpeI/XhoI restriction site in the downstream region and the antigen protein NS4 gene between them.

The purified PCR-amplified product was digested with BamHI and XhoI, and the digest was then inserted into the corresponding site of plasmid pGEX-6P-1 (Amersham Pharmacia Biotech), so as to obtain a vector pGEX-NS.

Then, *E. coli* expression vectors that can express each of the binding amino acid sequences (SEQ ID NOS: 1 to 15) of Example 1 fused to the N-terminus of the antigen protein NS4 via a spacer sequence GS were prepared as follows. A set of synthesized double-stranded oligonucleotides shown in Table 5 below was prepared as DNA encoding these amino acid sequences.

TABLE 5

Synthesized DNA used in expression of each amino acid sequence

| Amino acid sequence No. | Nucleotide sequence of synthesized DNA |
|---|---|
| 1 | 5'-GATCCAAATATGATAGCCGTCATCTGCATACCCATAGCCATGAGCT-3' |
| | 5'-CATGGCTATGGGTATGCACATGACGGCTATCATATTTG-3' |
| 2 | 5'-GATCCCCGAACCGTCTGGGCCGTCGTCCGGTGCGTTGGGAAGAGCT-3' |
| | 5'-CTTCCCAACGCACCGGACGACGGCCCAGACGGTTCGGG-3' |
| 3 | 5'-GATCCAAATGCTGCTATTATGATCATAGCCATGCGCTGAGCGAGCT-3' |
| | 5'-CGCTCAGCGCATGGCTATGATCATAATAGCAGCATTTG-3' |
| 4 | 5'-GATCCGAATATCTGAGCGCGATTGTGGCGGGCCCGTGGCCGGAGCT-3' |
| | 5'-CCGGCCACGGGCCCGCCACAATCGCGCTCAGATATTCG-3' |
| 5 | 5'-GATCCAAACTGTGGATTCTGGAACCGACCGTGACCCCGACCGAGCT-3' |
| | 5'-CGGTCGGGGTCACGGTCGGTTCCAGAATCCACAGTTTG-3' |
| 6 | 5'-GATCCCAGAGCAACCTGAAAGTGATTCCGAGCTGGTGGTTTGAGCT-3' |
| | 5'-CAAACCACCAGCTCGGAATCACTTTCAGGTTGCTCTGG-3' |
| 7 | 5'-GATCCTGGATTCCGCCGCAGTGGAGCCGTCTGATTGAACCGGAGCT-3' |
| | 5'-CCGGTTCAATCAGACGGCTCCACTGCGGCGGAATCCAG-3' |
| 8 | 5'-GATCCGATCATCCGCAGGCGAAACCGAACTGGTATGGCGTGGAGCT-3' |
| | 5'-CCACGCCATACCAGTTCGGTTTCGCCTGCGGATGATCG-3' |
| 9 | 5'-GATCCGGCCTGCCGCCGTATAGCCCGCATCGTCTGGCGCAGGAGCT-3' |
| | 5'-CCTGCGCCAGACGATGCGCGCTATACGCCGGCAGGCCG-3' |
| 10 | 5'-GATCCAAACTGACCACCCAGTATATGGCGCGTAGCAGCAGCGAGCT-3' |
| | 5'-CGCTGCTGCTACGCGCCATATACTGGGTGGTCAGTTTG-3' |

TABLE 5-continued Synthesized DNA used in expression of each amino acid sequence

| Amino acid sequence No. | Nucleotide sequence of synthesized DNA |
|---|---|
| 11 | 5'-GATCCAAAGTGTGGATGCTGCCGCCGCTGCCGCAGGCGACCGAGCT-3'<br><br>5'-CGGTCGCCTGCGGCAGCGGCGGCAGCATCCACACTTTG-3' |
| 12 | 5'-GATCCAACGTGACCAGCACCGCGTTTATTGATACCCCGTGGGAGCT-3'<br><br>5'-CCCACGGGGTATCAATAAACGCGCTGCTGGTCACGTTG-3' |
| 13 | 5'-GATCCCCTCTGAACCTGGATATTATTGCGGTGACCAGCGTGGAGCT-3'<br><br>5'-CCACGCTGGTCACCGCAATAATATCCAGGTTCAGACGG-3' |
| 14 | 5'-GATCCACCCTGCCGAGCCCGCTGGCGCTGCTGACCGTGCATGAGCT-3'<br><br>5'-CATGCACGGTCAGCAGCGCCAGCGGGCTCGGCAGGGTG-3' |
| 15 | 5'-GATCCACCAACCGTCATAACCCCCATCATCTGCATCATGTGGAGCT-3'<br><br>5'-CCACATGATGCAGATGATGCGGGTTATGACGGTTGGTG-3' |

(SEQ ID NO:43-72)

Two DNA fragments were synthesized for each amino acid sequence as shown in Table 5, and phosphorylated with T4 polynucleotide kinase (Gibco) according to the instructions of the manufacturers. Subsequently, the two synthesized DNA fragments were mixed in equimolar, and the mixture was heated at 80° C. for 5 minutes and slowly cooled to room temperature, so as to obtain a double-stranded DNA fragment. The obtained double-stranded DNA fragment was directly used in the following cloning step.

The plasmid pGEX-NS was digested with BamHI or SacI, and the above double-stranded DNA fragment was inserted thereinto. A host microorganism, E. coli JM109 was transformed using this vector, so as to obtain a transformant that expresses a binding amino acid sequence-NS4-glutathione-S-transferase (GST) fusion protein. The transformed strain was confirmed by determining the nucleotide sequence of the insert by sequencing using pGEX 5' Sequencing Primer (Amersham Pharmacia Biotech) and plasmid DNA prepared using Miniprep (Wizard Minipreps DNA Purification Systems (PROMEGA)) as a template.

The obtained strain was precultured overnight in 10 ml LB-Amp medium, and 0.1 ml of the preculture was transferred to fresh 10 ml LB-Amp medium for shake culture of 170 rpm at 37° C. for 3 hours. Thereafter, IPTG was added thereto (final concentration: 1 mM), and culture was continued at 37° C. for 4 to 12 hours.

IPTG-induced E. coli was collected (8,000×g, 2 minutes, 4° C.) and resuspended in a 1/10 amount of 4° C. PBS. The cells were disrupted by freezing-thawing and sonication, and centrifuged (8,000×g, 10 minutes, 4° C.) to remove solid matters. The presence of an expressed protein of interest in the supernatant was confirmed by SDS-PAGE, and thereafter, the expressed GST fusion protein was purified using Glutathione Sepharose 4B (Glutathione Sepharose 4B beads; Amersham Pharmacia Biotech).

Beforehand, the glutathione sepharose was treated for controlling nonspecific adsorption as follows: Glutathione sepharose was washed three times with an equal amount of PBS using centrifugation (8,000×g, 1 minute, 4° C.), to which an equal amount of 4% BSA-containing PBS was added, and then left to stand at 4° C. for 1 hour. After the treatment, the resulting product was washed twice with an equal amount of PBS, and it was then resuspended in a ½ amount of PBS.

40 µl of the pretreated glutathione sepharose was added to 1 ml of a cell-free extract, and the mixture was gently stirred at 4° C. Thus, the GST fusion protein was adsorbed on the glutathione sepharose.

After the adsorption, the glutathione sepharose was recovered by centrifugation (8,000×g, 1 minute, 4° C.), and washed three times with 400 µl of PBS. Thereafter, 40 µl of 10 mM glutathione was added thereto, and the mixture was stirred at 4° C. for 1 hour to elute the adsorbed GST fusion protein. The supernatant was recovered by centrifugation (8,000×g, 2 minutes, 4° C.), and dialyzed against PBS so as to purify the GST fusion protein. It was confirmed that the purified protein showed a single band on SDS-PAGE.

500 µg of each GST fusion protein was digested with PreScission protease (Amersham Pharmacia Biotech, 5 U), and the digest was passed through glutathione sepharose to remove the PreScission protease and the GST. The flow-through fraction was applied to a Sephadex G200 column equilibrated with PBS, so as to obtain the final purified product of the expression protein. It was confirmed that the final purified protein showed a single band on SDS-PAGE.

Example 4

Production of Antigen Protein Capable of Binding to Carbon Black

With an upstream primer (5'-TTCACAGGATCCACTGAGCTCGATGCC CAC-3') and an downstream primer (5'-GATCTGGGCTCGAGCCGACTAGTA GTCGCT-3') for a nucleotide sequence encoding the antigen protein NS4, PCR was carried out using the plasmid pUC18-NS prepared in Reference Example as a template. The obtained DNA fragment had BamHI and SacI restriction site in the upstream region and SpeI and XhoI restriction site in the downstream region and the antigen protein NS4 gene between them.

The purified PCR-amplified product was digested with BamHI and XhoI, and the digest was then inserted into the corresponding site of plasmid pGEX-6P-1 (Amersham Pharmacia Biotech), so as to obtain a vector pGEX-NS.

Then, E. coli expression vectors that can express each of the binding amino acid sequences (SEQ ID NOS: 16 to 40) of Example 2 fused to the N-terminus of the antigen protein NS4 via a spacer sequence GS were prepared as follows. A set of synthesized double-stranded oligonucleotides shown in Table 6 below was prepared as DNA encoding these amino acid sequences.

TABLE 6

Synthesized DNA sets used in expression of each amino acid sequence

| Amino acid sequence No. | Nucleotide sequence of synthesized DNA |
|---|---|
| 16 | 5'-GATCCTGGCCGCATGCGTGGAAAGTGTGGTGGCCGGCGAGCGAGCT-3' |
|  | 5'-CGCTCGCCGGCCACCACACTTTCCACGCATGCGGCCAG-3' |
| 17 | 5'-GATCCAACTGGTGGTGGCCGCCGTATATTCGTCATCAGCCGGAGCT-3' |
|  | 5'-CCGGCTGATGACGAATATACGGCGGCCACCACCAGTTG-3' |
| 18 | 5'-GATCCTGGCATTGGAGCTGGACCCCGTGGCCGAGCCATCATGAGCT-3' |
|  | 5'-CATGATGGCTCCGCCACGGGGTCCAGCTCCAATGCCAG-3' |
| 19 | 5'-GATCCTGGCCGTGGGCGTGGCATCCGAGCCGTGATGTGTATGAGCT-3' |
|  | 5'-CATACACATCACGGCTCGGATGCCACGCCCACGGCCAG-3' |
| 20 | 5'-GATCCTGGCATGGCTATTGGTATAGCAACCTGAACACCACCGAGCT-3' |
|  | 5'-CGGTGGTGTTCAGGTTGCTATACCAATAGCCATGCCAG-3' |
| 21 | 5'-GATCCTGGTGGACCCCGTGGATGAGCCATGCGTATCCGGTGGACT-3 |
|  | 5'-CCACCGGATACGCATGGCTCATCCACGGGGTCCACCAG-3 |
| 22 | 5'-GATCCTGGCCGAACCCGTATTGGGGCTGGTTTGCGGCGGTGGAGCT-3' |
|  | 5'-CCACCGCCGCAAACCAGCCCCAATACGGGTTCGGCCAG-3 |
| 23 | 5'-GATCCACCAGCTGGCATACCTGGTGGTGGCGTCAGCCGCCGGAGCT-3 |
|  | 5'-CCGGCGGCTGACGCCACCACCAGGTATGCCAGCTGGTG-3 |
| 24 | 5'-GATCCAACGCGTGGCATAAATATTGGTGGCCGATTACCAAAGAGCT-3' |
|  | 5'-CTTTGGTAATCGGCCACCAATATTTATGCCACGCGTTG-3' |
| 25 | 5'-GATCCCATCCGAACAACGATTGGAGCAAAGCGCCGCAGTTTGAGCT-3' |
|  | 5'-CAAACTGCGGCGCTTTGCTCCAATCGTTGTTCGGATGG-3' |
| 26 | 5'-GATCCTGGTGGACCCCGCAGCCGTGGTGGAGCTTTCCGATTGAGCT-3' |
|  | 5'-CAATCGGAAAGCTCCACCACGGCTGCGGGGTCCACCAG-3' |
| 27 | 5'-GATCCTGGCCGCATACCAGCTGGTGGCAGACCCCGCTGACCGAGCT-3 |
|  | 5'-CGGTCAGCGGGGTCTGCCACCAGCTGGTATGCGGCCAG-3' |
| 28 | 5'-GATCCTGGCATGTGAACTGGGATCCGATGGCGTGGTATCGTGAGCT-3' |
|  | 5'-CACGATACCACGCCATCGGATCCCAGTTCACATGCCAG-3' |
| 29 | 5'-GATCCAGCTGGCCGTGGTGGACCGCGTATCGTGTGCATAGCGAGCT-3' |
|  | 5'-CGCTATGCACACGATACGCGGTCCACCACGGCCAGCTG-3 |
| 30 | 5'-GATCCTGGCATAGCAACTGGTATCAGAGCATTCCGCAGGTGGAGCT-3' |
|  | 5'-CCACCTGCGGAATGCTCTGATACCAGTTGCTATGCCAG-3' |
| 31 | 5'-GATCCGGCTATTGGCCGTGGAAATTTGAACATGCGACCGTGGAGCT-3' |
|  | 5'-CCACGGTCGCATGTTCAAATTTCCACGGCCAATAGCCG-3' |
| 32 | 5'-GATCCGCGTGGTGGCCGACCACCTTTCCGCCGTATTATTATGAGCT-3' |
|  | 5'-CATAATAATACGGCGGAAAGGTGGTCGGCCACCACGCG-3' |
| 33 | 5'-GATCCAACCCGTGGTGGAGCCATTATTATCCGCGTAGCGTGGAGCT-3' |
|  | 5'-CCACGCTACGCCCATAATAATGGCTCCACCACGGGTTG-3' |
| 34 | 5'-GATCCTGGCCGCATAACTATCCGCTGAACCATAGCAACCCGGAGCT-3' |
|  | 5'-CCGGGTTGCTATGGTTCAGCGGATAGTTATGCGGCCAG-3' |
| 35 | 5'-GATCCACCTGGGCGCATCCGCTGGAAAGCGATTATCTGCGTGAGCT-3' |
|  | 5'-CACGCAGATAATCGCTTTCCAGCGGATGCGCCCAGGTG-3' |
| 36 | 5'-GATCCCATACCTATTATCATGATGGCTGGCGTCTGGCGCCGGAGCT-3' |
|  | 5'-CCGGCGCCAGACGCCAGCCATCATGATAATAGGTATGG-3' |
| 37 | 5'-GATCCACCTTTGTGCAGACCCCGCTGAGCCATCTGATTCCGGAGCT-3' |
|  | 5'-CCGCAATCAGATGGCTCAGCGGGGTCTGCACAAAGGTG-3 |
| 38 | 5'-GATCCCGTGTGCCGCCGAGCAAACTGACCCGTCCGCCGTTTGAGCT-3' |
|  | 5'-CAAACGGCGGACGGGTCAGTTTGCTCGGCGGCACACGG-3' |

TABLE 6-continued

Synthesized DNA sets used in expression of each amino acid sequence

| Amino acid sequence No. | Nucleotide sequence of synthesized DNA |
|---|---|
| 39 | 5'-GATCCCATAGCATTTATAGCGTGACCCCGAGCACCGCGAGCGAGCT-3' |
|  | 5'-CGCTCGCGGTGCTCGGGGTCACGCTATAAATGCTATGG-3' |
| 40 | 5'-GATCCCTGAACACCCAGAACCATGCGCCGCTGCCGAGCATTGAGCT-3' |
|  | 5'-CAATGCTCGGCAGCGGCGCATGGTTCTGGGTGTTCAGG-3' |

(SEQ ID NO:73-122)

Two DNA fragments were synthesized for each amino acid sequence as shown in Table 5, and phosphorylated with T4 polynucleotide kinase (Gibco) according to the instructions of the manufacturers. Subsequently, the two synthesized DNA fragments were mixed in equimolar, and the mixture was heated at 80° C. for 5 minutes and slowly cooled to room temperature, so as to obtain a double-stranded DNA fragment. The obtained double-stranded DNA fragment was directly used in the following cloning step.

The plasmid pGEX-NS was digested with BamHI or SacI, and the above double-stranded DNA fragment was inserted thereinto. A host microorganism, *E. coli* JM109 was transformed using this vector, so as to obtain a transformant that expresses a binding amino acid sequence-NS4-glutathione-S-transferase (GST) fusion protein. The transformant was confirmed by determining the nucleotide sequence of the insert by sequencing using pGEX 5' Sequencing Primer (Amersham Pharmacia Biotech) and plasmid DNA prepared using Minprep (Wizard Minipreps DNA Purification Systems (PROMEGA)) as a template.

The obtained strain was precultured overnight in 10 ml LB-Amp medium, and 0.1 ml of the preculture was transferred to fresh 10 ml LB-Amp medium for shake culture of 170 rpm at 37° C. for 3 hours. Thereafter, IPTG was added thereto (final concentration: 1 mM), and culture was continued at 37° C. for 4 to 12 hours.

IPTG-induced *E. coli* was collected (8,000×g, 2 minutes, 4° C.) and resuspended in a 1/10 amount of 4° C. PBS. The cells were disrupted by freezing-thawing and sonication, and centrifuged (8,000×g, 10 minutes, 4° C.) to remove solid matters. The presence of an expressed protein of interest in the supernatant was confirmed by SDS-PAGE, and thereafter, the expressed GST fusion protein was purified using Glutathione Sepharose 4B (Glutathione Sepharose 4B beads; Amersham Pharmacia Biotech).

Beforehand, the glutathione sepharose was treated for controlling nonspecific adsorption as follows: Glutathione sepharose was washed three times with an equal amount of PBS using centrifugation (8,000×g, 1 minute, 4° C.), to which an equal amount of 4% BSA-containing PBS was added, and then left to stand at 4° C. for 1 hour. After the treatment, the resulting product was washed twice with an equal amount of PBS, and it was then resuspended in a ½ amount of PBS.

40 µl of the pretreated glutathione sepharose was added to 1 ml of a cell-free extract, and the mixture was gently stirred at 4° C. Thus, the GST fusion protein was adsorbed on the glutathione sepharose.

After the adsorption, the glutathione sepharose was recovered by centrifugation (8,000×g, 1 minute, 4° C.), and washed three times with 400 µl of PBS. Thereafter, 40 µl of 10 mM glutathione was added thereto, and the mixture was stirred at 4° C. for 1 hour to elute the adsorbed GST fusion protein. The supernatant was recovered by centrifugation (8,000×g, 2 minutes, 4° C.), and dialyzed against PBS so as to purify the GST fusion protein. It was confirmed that the purified protein showed a single band on SDS-PAGE.

500 µg of each GST fusion protein was digested with PreScission protease (Amersham Pharmacia Biotech, 5 U), and the digest was passed through glutathione sepharose to remove the PreScission protease and the GST. The flow-through fraction was applied to a Sephadex G200 column equilibrated with PBS, so as to obtain the final purified product of the expression protein. It was confirmed that the final purified protein showed a single band on SDS-PAGE.

Example 5

Production of Antigen Protein Capable of Binding to Copper Phthalocyanine

Two types of amino acid sequences capable of binding to copper phthalocyanine, Lys-Tyr-Asp-Ser-Arg-His-Leu-His-Thr-His-Ser-His (SEQ ID NO 1) and Pro-Asn-Arg-Leu-Gly-Arg-Arg-Pro-Val-Arg-Trp-Glu (SEQ ID NO 2), are connected in tandem in this order via a spacer sequence (Gly-Gly-Gly-Ser-Gly-Gly-Gly-Ser), so as to obtain a sequence Lys-Tyr-Asp-Ser-Arg-His-Leu-His-Thr-His-Ser-His-Gly-Gly-Gly-Ser-Gly-Gly-Gly-Ser-Pro-Asn-Arg-Leu-Gly-Arg-Arg-Pro-Val-Arg-Trp-Glu (SEQ ID NO 41). Then, an *E. coli* expression vector was constructed as described below, which expresses the obtained amino acid sequence via the spacer sequence GS such that the amino acid sequence is fused with the N-terminus of the antigen protein NS4. DNA encoding this amino acid sequence was obtained as a double-stranded DNA fragment as follows: each of two types of synthetic oligonucleotides,

5'-GATCCAAATATGATAGCCGTCATCTGCATACCCATAGCCATGGCGGCGGCAGC (SEQ ID NO:123)

GGCGGCGGCAGCCCGAACCGTCTGGGCCGTCGTCCGGTGCGTTGGGAAGAGCT-3'
and

5'-CTTCCCAACGCACCGGACGACGGCCCAGACGGTTCGGGCTGCCGCCGCCGCTG (SEQ ID NO:124)

CCGCCGCCATGGCTATGGGTATGCAGATGACGGCTATCATATTTG-3' was phosphorylated with T4 polynucleotide kinase (Gibco), and mixed equimolar, and the mixture was heated at 80° C. for 5 minutes and then slowly cooled to room temperature. The obtained double-stranded DNA fragment was inserted into the BamHI/SacI site of plasmid pGEX-NS in the same manner as in Example 3. Using this vector, E. coli JM109 was transformed to obtain an expression transformant. In the same manner as in Example 3, an expression protein in which the amino acid sequence of SEQ ID NO 41 was fused at N-terminus of NS 4 was purified.

Example 6

Production of Antigen Protein Capable of Binding to Carbon Black

Two types of amino acid sequences capable of binding to carbon black, Trp-Pro-His-Ala-Trp-Lys-Val-Trp-Trp-Pro-Ala-Ser (SEQ ID NO 16) and Asn-Trp-Trp-Trp-Pro-Pro -Tyr-Ile-Arg-His-Gln-Pro-(SEQ ID NO 17), are connected tandem in this order via a spacer sequence (Gly-Gly-Gly-Ser-Gly-Gly-Gly-Ser), so as to obtain a sequence Trp-Pro-His-Ala-Trp-Lys-Val-Trp-Trp-Pro-Ala-Ser-Gly-Gly-Gly-Ser-Gly-Gly-Gly-Ser-Asn-Trp-Trp-Trp-Pro-Pro -Tyr-Ile-Arg-His-Gln-Pro- (SEQ ID NO 42). Then, an *E. coli* expression vector was constructed as described below, which expresses the obtained amino acid sequence via the spacer sequence GS such that the amino acid sequence is fused to the N-terminus of the antigen protein NS4. DNA encoding this amino acid sequence was obtained as a double-stranded DNA fragment as follows. Each of two types of synthetic oligonucleotides, 5'-GATCCTGGCCCGCATGCGTGGAAAGT-GTGGTGGCCGGCGAGCGGCGGCGGCAGC GGCG-GCGGCAGCAACTGGTGGTGGCCGCCG-TATATTCGTCATCAGCCGGAGCT-3' (SEQ ID NO:125) and 5'-CCGGCTGATGACGAATATACGGCGGC-CACCACCAGTTGCTGCCGCCGCCGCTG CCGCCGC-CGCTCGCCGGCCACCACACTTTCCACG-CATGCGGCCAG-3' (SEQ ID NO:126) was phosphorylated with T4 polynucleotide kinase (Gibco), and mixed in equimolar, the mixture was heated at 80° C. for 5 minutes and slowly cooled to room temperature. The obtained double-stranded DNA fragment was inserted into the BamHI/SacI site of plasmid pGEX-NS in the same manner as in Example 4. Using this vector, *E coli* JM109 was transformed to obtain an expression transformant. In the same manner as in Example 4, an expression protein in which the amino acid sequence of SEQ ID NO 42 was fused at N-terminus of NS4 was purified.

Comparative Example 1

Production of Antigen Protein

With an upstream primer (5'-TTCACAGGATCCACT-GAGCTCGATGCC CAC-3') and an downstream primer (5'-GATCTGGGCTCGAGCCGACTAGTA GTCGCT-3') for a nucleotide sequence encoding the antigen protein NS4, PCR was carried out using the plasmid pUC18-NS prepared in Reference Example as a template. The obtained DNA fragment had BamHI and SacI restriction site in the upstream region and SpeI and XhoI restriction site in the downstream region and the antigen protein NS4 gene between them.

The purified PCR-amplified product was digested with BamHI and XhoI, and the digest was then inserted into the corresponding site of plasmid pGEX-6P-1 (Amersham Pharmacia Biotech), so as to obtain a vector pGEX-NS. Using this vector, *E. coli* JM109 was transformed so as to obtain a transformed strain for the expression of an NS4-GST fusion protein. The transformant was confirmed by determining the nucleotide sequence of the insert by sequencing using pGEX 5' Sequencing Primer (Amersham Pharmacia Biotech) and plasmid DNA prepared using Miniprep (Wizard Minipreps DNA Purification Systems (PROMEGA)) as a template.

The obtained strain was precultured overnight in 10 ml LB-Amp medium, and 0.1 ml of the preculture was transferred to fresh 10 ml LB-Amp medium for shake culture of 170 rpm at 37° C. for 3 hours. Thereafter, IPTG was added thereto (final concentration: 1 mM), and culture was continued at 37° C. for 4 to 12 hours.

IPTG-induced *E. coli* was collected (8,000×g, 2 minutes, 4° C.) and resuspended in a 1/10 amount of 4° C. PBS. The cells were disrupted by freezing-thawing and sonication, and centrifuged (8,000×g, 10 minutes, 4° C.) to remove solid matters. The presence of an expressed protein of interest in the supernatant was confirmed by SDS-PAGE, and thereafter, the expressed GST fusion protein was purified using Glutathione Sepharose 4B (Glutathione Sepharose 4B beads; Amersham Pharmacia Biotech).

Beforehand, the glutathione sepharose was treated for controlling nonspecific adsorption as follows: Glutathione sepharose was washed three times with an equal amount of PBS using centrifugation (8,000×g, 1 minute, 4° C.), to which an equal amount of 4% BSA-containing PBS was added, and then left to stand at 4° C. for 1 hour. After the treatment, the resulting product was washed twice with an equal amount of PBS, and it was then resuspended in a ½ amount of PBS.

40 μl of the pretreated glutathione sepharose was added to 1 ml of a cell-free extract, and the mixture was gently stirred at 4° C. Thus, the GST fusion protein was adsorbed on the glutathione sepharose.

After the adsorption, the glutathione sepharose was recovered by centrifugation (8,000×g, 1 minute, 4° C.), and washed three times with 400 μl of PBS. Thereafter, 40 μl of 10 mM glutathione was added thereto, and the mixture was stirred at 4° C. for 1 hour to elute the adsorbed GST fusion protein. The supernatant was recovered by centrifugation (8,000×g, 2 minutes, 4° C.), and dialyzed against PBS so as to purify the GST fusion protein. It was confirmed that the purified protein showed a single band on SDS-PAGE.

500 μg of each GST fusion protein was digested with PreScission protease (Amersham Pharmacia Biotech, 5 U), and the digest was passed through glutathione sepharose to remove the PreScission protease and the GST. The flow-through fraction was applied to a Sephadex G200 column equilibrated with PBS, so as to obtain the final purified product of the expression protein. It was confirmed that the final purified protein showed a single band on SDS-PAGE.

Example 7

Immobilization of Antigen Protein on Copper Phthalocyanine Particle

Copper phthalocyanine particles were suspended in a TBS buffer containing 0.1% Tween-20 to a concentration of 0.5% (w/v). 10 ml of the suspension was placed in a Teflon (Commercial name) centrifugation tube, and 50 μg of the fusion protein prepared in Example 3 and 5, or the same amount of the protein prepared in Comparative Example 1 was added thereto followed by shaking at room temperature for 30 minutes. Centrifugal separation (10,000×g, 4° C., 10 minutes) was carried out, and copper phthalocyanine particles were recovered as a precipitate, so that the precipitate was separated from the supernatant containing antigen that did not bind to the copper phthalocyanine particles. The copper phthalocyanine particles were resuspended in a TBS buffer containing 0.1% Tween-20, and centrifugal separation was repeatedly carried out so as to wash the copper phthalocyanine particles. The protein concentration of the suspension of the washed copper phthalocyanine particles was determined with a Micro BCA Protein Assay Reagent (Pierce Chemical). The results are shown in Table 7.

TABLE 7

Evaluation of binding ability of enzyme to copper phthalocyanine

| | Amino acid sequence No. | Amount of protein (µg) |
|---|---|---|
| Example 3 | 1 | 6 |
| Example 3 | 2 | 6 |
| Example 3 | 3 | 5 |
| Example 3 | 4 | 5 |
| Example 3 | 5 | 5 |
| Example 3 | 6 | 5 |
| Example 3 | 7 | 5 |
| Example 3 | 8 | 5 |
| Example 3 | 9 | 5 |
| Example 3 | 10 | 5 |
| Example 3 | 11 | 5 |
| Example 3 | 12 | 5 |
| Example 3 | 13 | 5 |
| Example 3 | 14 | 4 |
| Example 3 | 15 | 4 |
| Example 5 | 41 | 11 |
| Comparative example 1 | — | 1 |

The concentration of the fusion proteins of Examples 3 and 5, with which a copper phthalocyanine binding sequence was fused, was higher than the concentration of the protein of Comparative Example 1. Thus, it was confirmed that an antigen protein can effectively be immobilized on the surface of a pigment by the fusion protein.

Example 8

Immobilization of Antigen Protein on Carbon Black Article

Carbon black particles were suspended in a TBS buffer containing 0.1% Tween-20, at a concentration of 0.5% (w/v). 10 ml of the suspension was placed in a Teflon (commercial name) centrifugation tube, and 50 µg of the fusion protein prepared in Example 4 and 6, or the same amount of the protein prepared in Comparative Example 1 was added thereto followed by shaking at room temperature for 30 minutes. Centrifugal separation (10,000×g, 4° C., 10 minutes) was carried out, and carbon black particles were recovered as a precipitate, so that the precipitate was separated from the supernatant containing antigen that did not bind to the carbon black particles. The carbon black particles were resuspended in a TBS buffer containing 0.1% Tween-20, and centrifugal separation was repeatedly carried out so as to wash the carbon black particles. The protein concentration of the suspension of the washed carbon black particles was determined with a Micro BCA Protein Assay Reagent (Pierce Chemical). The results are shown in Table 8.

TABLE 8

Evaluation, of binding ability of enzyme to carbon black

| | Amino acid sequence No. | Amount of protein (µg) |
|---|---|---|
| Example 4 | 16 | 6 |
| Example 4 | 17 | 6 |
| Example 4 | 18 | 5 |
| Example 4 | 19 | 5 |
| Example 4 | 20 | 5 |
| Example 4 | 21 | 5 |

TABLE 8-continued

Evaluation, of binding ability of enzyme to carbon black

| | Amino acid sequence No. | Amount of protein (µg) |
|---|---|---|
| Example 4 | 22 | 5 |
| Example 4 | 23 | 5 |
| Example 4 | 24 | 5 |
| Example 4 | 25 | 5 |
| Example 4 | 26 | 5 |
| Example 4 | 27 | 5 |
| Example 4 | 28 | 5 |
| Example 4 | 29 | 4 |
| Example 4 | 30 | 4 |
| Example 4 | 31 | 4 |
| Example 4 | 32 | 4 |
| Example 4 | 33 | 4 |
| Example 4 | 34 | 4 |
| Example 4 | 35 | 4 |
| Example 4 | 36 | 4 |
| Example 4 | 37 | 4 |
| Example 4 | 38 | 4 |
| Example 4 | 39 | 4 |
| Example 4 | 30 | 4 |
| Example 6 | 42 | 15 |
| Comparative example 1 | — | 1 |

The concentration of the fusion proteins of Examples 4 and 6 containing a carbon black binding sequence was higher than the concentration of the protein of Comparative Example 1. Thus, it was confirmed that an antigen protein could be effectively immobilized on the surface of a pigment by the fusion protein.

Example 9

Assay of HCV Antibody by Immunoagglutination Assay

Pigment particles on which each of the fusion proteins produced in Examples 7 and 8 was immobilized, were suspended in a blocking buffer consisting of a 0.1 M potassium phosphate buffer (pH 6.5), 1.0% bovine serum albumin (Sigma-Aldrich Japan, K.K.) and 0.05% $NaN_3$. The pigment particles were then recovered by centrifugal separation (10,000×g, 4° C., 10 minutes). This operation was repeated three times for washing. The obtained product was then suspended in 4 ml of a blocking buffer.

The above prepared assay reagent was compared with a commercially available diagnostic agent for immunoagglutination assay (Ortho HCV Ab PAII manufactured by Ortho Diagnostic Systems Inc., hereinafter referred to as a "commercially available product"), using the serum of HCV antibody positive patients. The test was carried out according to the manual attached to the above commercially available product. Results are shown in Tables 9 and 10.

TABLE 9

Assay results of serum of HCV antibody positive patients

| | Amino acid sequence No. | Dilution of serum (times) | | | |
|---|---|---|---|---|---|
| | | 10,000 | 25,000 | 50,000 | 100,000 |
| Example 7 | 1 | + | + | + | − |
| | 2 | + | + | + | − |
| | 3 | + | + | + | − |

TABLE 9-continued

Assay results of serum of HCV antibody positive patients

| Amino acid sequence No. | Dilution of serum (times) | | | |
|---|---|---|---|---|
| | 10,000 | 25,000 | 50,000 | 100,000 |
| 4 | + | + | + | − |
| 5 | + | + | + | − |
| 6 | + | + | + | − |
| 7 | + | + | + | − |
| 8 | + | + | + | − |
| 9 | + | + | + | − |
| 10 | + | + | + | − |
| 11 | + | + | + | − |
| 12 | + | + | + | − |
| 13 | + | + | + | − |
| 14 | + | + | + | − |
| 15 | + | + | + | − |
| 41 | + | + | + | − |
| Commercially available product | − | + | + | − | − |

(In the table, + means that agglutination is observed, and − means that no agglutination is observed.)

TABLE 10

Assay results of serum of Hepatitis C virus antibody positive patients

| | Amino acid sequence No. | Dilution of serum (times) | | | |
|---|---|---|---|---|---|
| | | 10,000 | 25,000 | 50,000 | 100,000 |
| Example 8 | 16 | + | + | + | − |
| | 17 | + | + | + | − |
| | 18 | + | + | + | − |
| | 19 | + | + | + | − |
| | 20 | + | + | + | − |
| | 21 | + | + | + | − |
| | 22 | + | + | + | − |

TABLE 10-continued

Assay results of serum of Hepatitis C virus antibody positive patients

| Amino acid sequence No. | Dilution of serum (times) | | | |
|---|---|---|---|---|
| | 10,000 | 25,000 | 50,000 | 100,000 |
| 23 | + | + | + | − |
| 24 | + | + | + | − |
| 25 | + | + | + | − |
| 26 | + | + | + | − |
| 27 | + | + | + | − |
| 28 | + | + | + | − |
| 29 | + | + | + | − |
| 30 | + | + | + | − |
| 31 | + | + | + | − |
| 32 | + | + | + | − |
| 33 | + | + | + | − |
| 34 | + | + | + | − |
| 35 | + | + | + | − |
| 36 | + | + | + | − |
| 37 | + | + | + | − |
| 38 | + | + | + | − |
| 39 | + | + | + | − |
| 40 | + | + | + | − |
| 42 | + | + | + | − |
| Commercially available product | − | + | + | − | − |

(In the table, + means that agglutination is observed, and − means that no agglutination is observed.)

From the results shown in Tables 9 and 10, it was found that the assay reagent of the present invention has sensitivity the same as or higher than the commercially available product. Moreover, since the assay reagent of the present invention contains a pigment as an insoluble carrier, the reagent is colored which enables extremely easy visual determination.

It should be noted that the assay was carried out by visual observation in the above examples, but agglutination state may also be assayed by visual image recognition means such as CCD. In such a case, the assay of agglutination state can be carried out without using a color material as a carrier.

---

What is claimed is:

1. An assay method for determining a presence or an amount of a target antibody or antigen in a specimen comprising the steps of:

preparing a carrier on which an antigen or antibody corresponding to the target antibody or antigen in said specimen respectively is immobilized;

mixing said carrier with said specimen; and assaying a level of an immunological agglutination reaction caused by said mixing step, wherein said antigen or antibody is immobilized by adsorptive binding to said carrier via an amino acid sequence covalently fused onto said antigen or antibody, wherein the amino acid sequence comprises at least one sequence selected from the group consisting of:

```
                                              (SEQ ID NO 1)
Lys-Tyr-Asp-Ser-Arg-His-Leu-His-Thr-His-Ser-His;

(SEQ ID NO 2)
Pro-Asn-Arg-Leu-Gly-Arg-Arg-Pro-Val-Arg-Trp-Glu;

(SEQ ID NO 3)
Lys-Cys-Cys-Tyr-Tyr-Asp-His-Ser-His-Ala-Leu-Ser;

(SEQ ID NO 4)
Glu-Tyr-Leu-Ser-Ala-Ile-Val-Ala-Gly-Pro-Trp-Pro;

(SEQ ID NO 5)
Lys-Leu-Trp-Ile-Leu-Glu-Pro-Thr-Val-Thr-Pro-Thr;

(SEQ ID NO 6)
Gln-Ser-Asn-Leu-Lys-Val-Ile-Pro-Ser-Trp-Trp-Phe;

(SEQ ID NO 7)
Trp-Ile-Pro-Pro-Gln-Trp-Ser-Arg-Leu-Ile-Glu-Pro;

(SEQ ID NO 8)
Asp-His-Pro-Gln-Ala-Lys-Pro-Asn-Trp-Tyr-Gly-Val;

(SEQ ID NO 9)
Gly-Leu-Pro-Pro-Tyr-Ser-Pro-His-Arg-Leu-Ala-Gln;

(SEQ ID NO 10)
Lys-Leu-Thr-Thr-Gln-Tyr-Met-Ala-Arg-Ser-Ser-Ser;

(SEQ ID NO 11)
Lys-Val-Trp-Met-Leu-Pro-Pro-Leu-Pro-Gln-Ala-Thr;

(SEQ ID NO 12)
Asn-Val-Thr-Ser-Thr-Ala-Phe-Ile-Asp-Thr-Pro-Trp;

(SEQ ID NO 13)
Arg-Leu-Asn-Leu-Asp-Ile-Ile-Ala-Val-Thr-Ser-Val;

(SEQ ID NO 14)
Thr-Leu-Pro-Ser-Pro-Leu-Ala-Leu-Leu-Thr-Val-Val;
and
                                             (SEQ ID NO 15)
Thr-Asn-Arg-His-Asn-Pro-His-His-Leu-His-His-Val,
``` and wherein said carrier is copper phthalocyanine.

\* \* \* \* \*

UNITED STATES PATENT AND TRADEMARK OFFICE
CERTIFICATE OF CORRECTION

| | |
|---|---|
| PATENT NO. | : 7,399,644 B2 |
| APPLICATION NO. | : 10/453483 |
| DATED | : July 15, 2008 |
| INVENTOR(S) | : Tsutomu Honma et al. |

It is certified that error appears in the above-identified patent and that said Letters Patent is hereby corrected as shown below:

ON THE TITLE PAGE ITEM -56-:
 Other Publications, After "A Particle", "Coagulase-nagative" should read -- Coagulase-negative --.

COLUMN 1:
 Line 43, "not necessarily requires" should read -- does not necessarily require --;
 Line 52, "so that" should be deleted; and
 Line 60, "antibody" should read -- an antibody --.

COLUMN 2:
 Line 6, "difference" should read -- differences --;
 Line 14, "can be applied not" should read -- cannot be applied --; and
 Line 29, "completed" should read -- completing --.

COLUMN 3:
 Line 52, "above described" should read -- above-described --.

COLUMN 4:
 Line 22, "above described" should read -- above-described --.

COLUMN 5:
 Line 9, "interfere" should read -- interfere with --;
 Line 27, "interfere" should read -- interfere with --;
 Line 59, "3-[(chloamidopropyl)dim-" should read -- 3-[(cholamidopropyl)dim- --; and
 Line 60, "3-[(3-chloa-" should read -- 3-[(3-chola- --.

COLUMN 11:
 Line 46, "an" should read -- a downstream --.

COLUMN 14:
 Line 47, "an" should read -- a downstream --.

UNITED STATES PATENT AND TRADEMARK OFFICE
CERTIFICATE OF CORRECTION

PATENT NO.       : 7,399,644 B2
APPLICATION NO.  : 10/453483
DATED            : July 15, 2008
INVENTOR(S)      : Tsutomu Honma et al.

It is certified that error appears in the above-identified patent and that said Letters Patent is hereby corrected as shown below:

COLUMN 15:
    Sequence No. 21, "CT-3" should read -- CT-3' --;
    Sequence No. 21, "CAG-3" should read -- CAG-3' --;
    Sequence No. 22, "CAG-3" should read -- CAG-3' --;
    Sequence No. 23, "CT-3" should read -- CT-3' --;
    Sequence No. 23, "GTG-3" should read -- GTG-3' --; and
    Sequence No. 27, "CT-3" should read -- CT-3' --.

COLUMN 16:
    Sequence No. 29, "CTG-3" should read -- CTG-3' --; and
    Sequence No. 37, "GTG-3" should read -- GTG-3' --.

COLUMN 19:
    Line 18, "-Pro  -Tyr-" should read -- -Pro-Tyr- --;
    Line 27, "C  GGCG-" should read -- CGGCG- --;
    Line 31, "G  CCGCCGC-" should read -- GCCGCCGC- --; and
    Line 49, "an downstream" should read -- a downstream --.

COLUMN 20:
    Line 55, "Example" should read -- Examples --.

COLUMN 21:
    Line 41, "Example" should read -- Examples --.

COLUMN 22:
    Table 8, "Example 4   30" should read -- Example 4   40 --.

UNITED STATES PATENT AND TRADEMARK OFFICE
CERTIFICATE OF CORRECTION

PATENT NO. : 7,399,644 B2
APPLICATION NO. : 10/453483
DATED : July 15, 2008
INVENTOR(S) : Tsutomu Honma et al.

It is certified that error appears in the above-identified patent and that said Letters Patent is hereby corrected as shown below:

COLUMN 66:
Line 29, "Val-Val;" should read -- Val-His; --.

Signed and Sealed this

Tenth Day of March, 2009

JOHN DOLL
*Acting Director of the United States Patent and Trademark Office*

SEQUENCE LISTING

```
<160> NUMBER OF SEQ ID NOS: 129

<210> SEQ ID NO 1
<211> LENGTH: 12
<212> TYPE: PRT
<213> ORGANISM: Artificial
<220> FEATURE:
<223> OTHER INFORMATION: binding peptide

<400> SEQUENCE: 1

Lys Tyr Asp Ser Arg His Leu His Thr His Ser His
1               5                   10

<210> SEQ ID NO 2
<211> LENGTH: 12
<212> TYPE: PRT
<213> ORGANISM: Artificial
<220> FEATURE:
<223> OTHER INFORMATION: binding peptide
```

```
<400> SEQUENCE: 2

Pro Asn Arg Leu Gly Arg Arg Pro Val Arg Trp Glu
1               5                   10

<210> SEQ ID NO 3
<211> LENGTH: 12
<212> TYPE: PRT
<213> ORGANISM: Artificial
<220> FEATURE:
<223> OTHER INFORMATION: binding peptide

<400> SEQUENCE: 3

Lys Cys Cys Tyr Tyr Asp His Ser His Ala Leu Ser
1               5                   10

<210> SEQ ID NO 4
<211> LENGTH: 12
<212> TYPE: PRT
<213> ORGANISM: Artificial
<220> FEATURE:
<223> OTHER INFORMATION: binding peptide

<400> SEQUENCE: 4

Glu Tyr Leu Ser Ala Ile Val Ala Gly Pro Trp Pro
1               5                   10

<210> SEQ ID NO 5
<211> LENGTH: 12
<212> TYPE: PRT
<213> ORGANISM: Artificial
<220> FEATURE:
<223> OTHER INFORMATION: binding peptide

<400> SEQUENCE: 5

Lys Leu Trp Ile Leu Glu Pro Thr Val Thr Pro Thr
1               5                   10

<210> SEQ ID NO 6
<211> LENGTH: 12
<212> TYPE: PRT
<213> ORGANISM: Artificial
<220> FEATURE:
<223> OTHER INFORMATION: binding peptide

<400> SEQUENCE: 6

Gln Ser Asn Leu Lys Val Ile Pro Ser Trp Trp Phe
1               5                   10

<210> SEQ ID NO 7
<211> LENGTH: 12
<212> TYPE: PRT
<213> ORGANISM: Artificial
<220> FEATURE:
<223> OTHER INFORMATION: binding peptide

<400> SEQUENCE: 7

Trp Ile Pro Pro Gln Trp Ser Arg Leu Ile Glu Pro
1               5                   10

<210> SEQ ID NO 8
<211> LENGTH: 12
<212> TYPE: PRT
<213> ORGANISM: Artificial
<220> FEATURE:
<223> OTHER INFORMATION: binding peptide

<400> SEQUENCE: 8
```

```
Asp His Pro Gln Ala Lys Pro Asn Trp Tyr Gly Val
1               5                   10
```

<210> SEQ ID NO 9
<211> LENGTH: 12
<212> TYPE: PRT
<213> ORGANISM: Artificial
<220> FEATURE:
<223> OTHER INFORMATION: binding peptide

<400> SEQUENCE: 9

```
Gly Leu Pro Pro Tyr Ser Pro His Arg Leu Ala Gln
1               5                   10
```

<210> SEQ ID NO 10
<211> LENGTH: 12
<212> TYPE: PRT
<213> ORGANISM: Artificial
<220> FEATURE:
<223> OTHER INFORMATION: binding peptide

<400> SEQUENCE: 10

```
Lys Leu Thr Thr Gln Tyr Met Ala Arg Ser Ser Ser
1               5                   10
```

<210> SEQ ID NO 11
<211> LENGTH: 12
<212> TYPE: PRT
<213> ORGANISM: Artificial
<220> FEATURE:
<223> OTHER INFORMATION: binding peptide

<400> SEQUENCE: 11

```
Lys Val Trp Met Leu Pro Pro Leu Pro Gln Ala Thr
1               5                   10
```

<210> SEQ ID NO 12
<211> LENGTH: 12
<212> TYPE: PRT
<213> ORGANISM: Artificial
<220> FEATURE:
<223> OTHER INFORMATION: binding peptide

<400> SEQUENCE: 12

```
Asn Val Thr Ser Thr Ala Phe Ile Asp Thr Pro Trp
1               5                   10
```

<210> SEQ ID NO 13
<211> LENGTH: 12
<212> TYPE: PRT
<213> ORGANISM: Artificial
<220> FEATURE:
<223> OTHER INFORMATION: binding peptide

<400> SEQUENCE: 13

```
Arg Leu Asn Leu Asp Ile Ile Ala Val Thr Ser Val
1               5                   10
```

<210> SEQ ID NO 14
<211> LENGTH: 12
<212> TYPE: PRT
<213> ORGANISM: Artificial
<220> FEATURE:
<223> OTHER INFORMATION: binding peptide

<400> SEQUENCE: 14

```
Thr Leu Pro Ser Pro Leu Ala Leu Leu Thr Val His
1               5                   10
```

<210> SEQ ID NO 15
<211> LENGTH: 12
<212> TYPE: PRT
<213> ORGANISM: Artificial
<220> FEATURE:
<223> OTHER INFORMATION: binding peptide

<400> SEQUENCE: 15

```
Thr Asn Arg His Asn Pro His His Leu His His Val
1               5                   10
```

<210> SEQ ID NO 16
<211> LENGTH: 12
<212> TYPE: PRT
<213> ORGANISM: Artificial
<220> FEATURE:
<223> OTHER INFORMATION: binding peptide

<400> SEQUENCE: 16

```
Trp Pro His Ala Trp Lys Val Trp Trp Pro Ala Ser
1               5                   10
```

<210> SEQ ID NO 17
<211> LENGTH: 12
<212> TYPE: PRT
<213> ORGANISM: Artificial
<220> FEATURE:
<223> OTHER INFORMATION: binding peptide

<400> SEQUENCE: 17

```
Asn Trp Trp Trp Pro Pro Tyr Ile Arg His Gln Pro
1               5                   10
```

<210> SEQ ID NO 18
<211> LENGTH: 12
<212> TYPE: PRT
<213> ORGANISM: Artificial
<220> FEATURE:
<223> OTHER INFORMATION: binding peptide

<400> SEQUENCE: 18

```
Trp His Trp Ser Trp Thr Pro Trp Pro Ser His His
1               5                   10
```

<210> SEQ ID NO 19
<211> LENGTH: 12
<212> TYPE: PRT
<213> ORGANISM: Artificial
<220> FEATURE:
<223> OTHER INFORMATION: binding peptide

<400> SEQUENCE: 19

```
Trp Pro Trp Ala Trp His Pro Ser Arg Asp Val Tyr
1               5                   10
```

<210> SEQ ID NO 20
<211> LENGTH: 12
<212> TYPE: PRT
<213> ORGANISM: Artificial
<220> FEATURE:
<223> OTHER INFORMATION: binding peptide

<400> SEQUENCE: 20

```
Trp His Gly Tyr Trp Tyr Ser Asn Leu Asn Thr Thr
```

<210> SEQ ID NO 21
<211> LENGTH: 12
<212> TYPE: PRT
<213> ORGANISM: Artificial
<220> FEATURE:
<223> OTHER INFORMATION: binding peptide

<400> SEQUENCE: 21

Trp Trp Thr Pro Trp Met Ser His Ala Tyr Pro Val
1               5                   10

<210> SEQ ID NO 22
<211> LENGTH: 12
<212> TYPE: PRT
<213> ORGANISM: Artificial
<220> FEATURE:
<223> OTHER INFORMATION: binding peptide

<400> SEQUENCE: 22

Trp Pro Asn Pro Tyr Trp Gly Trp Phe Ala Ala Val
1               5                   10

<210> SEQ ID NO 23
<211> LENGTH: 12
<212> TYPE: PRT
<213> ORGANISM: Artificial
<220> FEATURE:
<223> OTHER INFORMATION: binding peptide

<400> SEQUENCE: 23

Thr Ser Trp His Thr Trp Trp Trp Arg Gln Pro Pro
1               5                   10

<210> SEQ ID NO 24
<211> LENGTH: 12
<212> TYPE: PRT
<213> ORGANISM: Artificial
<220> FEATURE:
<223> OTHER INFORMATION: binding peptide

<400> SEQUENCE: 24

Asn Ala Trp His Lys Tyr Trp Trp Pro Ile Thr Lys
1               5                   10

<210> SEQ ID NO 25
<211> LENGTH: 12
<212> TYPE: PRT
<213> ORGANISM: Artificial
<220> FEATURE:
<223> OTHER INFORMATION: binding peptide

<400> SEQUENCE: 25

His Pro Asn Asn Asp Trp Ser Lys Ala Pro Gln Phe
1               5                   10

<210> SEQ ID NO 26
<211> LENGTH: 12
<212> TYPE: PRT
<213> ORGANISM: Artificial
<220> FEATURE:
<223> OTHER INFORMATION: binding peptide

<400> SEQUENCE: 26

Trp Trp Thr Pro Gln Pro Trp Trp Ser Phe Pro Ile
1               5                   10

```
<210> SEQ ID NO 27
<211> LENGTH: 12
<212> TYPE: PRT
<213> ORGANISM: Artificial
<220> FEATURE:
<223> OTHER INFORMATION: binding peptide

<400> SEQUENCE: 27

Trp Pro His Thr Ser Trp Trp Gln Thr Pro Leu Thr
1               5                   10

<210> SEQ ID NO 28
<211> LENGTH: 12
<212> TYPE: PRT
<213> ORGANISM: Artificial
<220> FEATURE:
<223> OTHER INFORMATION: binding peptide

<400> SEQUENCE: 28

Trp His Val Asn Trp Asp Pro Met Ala Trp Tyr Arg
1               5                   10

<210> SEQ ID NO 29
<211> LENGTH: 12
<212> TYPE: PRT
<213> ORGANISM: Artificial
<220> FEATURE:
<223> OTHER INFORMATION: binding peptide

<400> SEQUENCE: 29

Ser Trp Pro Trp Trp Thr Ala Tyr Arg Val His Ser
1               5                   10

<210> SEQ ID NO 30
<211> LENGTH: 12
<212> TYPE: PRT
<213> ORGANISM: Artificial
<220> FEATURE:
<223> OTHER INFORMATION: binding peptide

<400> SEQUENCE: 30

Trp His Ser Asn Trp Tyr Gln Ser Ile Pro Gln Val
1               5                   10

<210> SEQ ID NO 31
<211> LENGTH: 12
<212> TYPE: PRT
<213> ORGANISM: Artificial
<220> FEATURE:
<223> OTHER INFORMATION: binding peptide

<400> SEQUENCE: 31

Gly Tyr Trp Pro Trp Lys Phe Glu His Ala Thr Val
1               5                   10

<210> SEQ ID NO 32
<211> LENGTH: 12
<212> TYPE: PRT
<213> ORGANISM: Artificial
<220> FEATURE:
<223> OTHER INFORMATION: binding peptide

<400> SEQUENCE: 32

Ala Trp Trp Pro Thr Thr Phe Pro Pro Tyr Tyr Tyr
1               5                   10
```

```
<210> SEQ ID NO 33
<211> LENGTH: 12
<212> TYPE: PRT
<213> ORGANISM: Artificial
<220> FEATURE:
<223> OTHER INFORMATION: binding peptide

<400> SEQUENCE: 33

Asn Pro Trp Trp Ser His Tyr Tyr Pro Arg Ser Val
1               5                   10

<210> SEQ ID NO 34
<211> LENGTH: 12
<212> TYPE: PRT
<213> ORGANISM: Artificial
<220> FEATURE:
<223> OTHER INFORMATION: binding peptide

<400> SEQUENCE: 34

Trp Pro His Asn Tyr Pro Leu Asn His Ser Asn Pro
1               5                   10

<210> SEQ ID NO 35
<211> LENGTH: 12
<212> TYPE: PRT
<213> ORGANISM: Artificial
<220> FEATURE:
<223> OTHER INFORMATION: binding peptide

<400> SEQUENCE: 35

Thr Trp Ala His Pro Leu Glu Ser Asp Tyr Leu Arg
1               5                   10

<210> SEQ ID NO 36
<211> LENGTH: 12
<212> TYPE: PRT
<213> ORGANISM: Artificial
<220> FEATURE:
<223> OTHER INFORMATION: binding peptide

<400> SEQUENCE: 36

His Thr Tyr Tyr His Asp Gly Trp Arg Leu Ala Pro
1               5                   10

<210> SEQ ID NO 37
<211> LENGTH: 12
<212> TYPE: PRT
<213> ORGANISM: Artificial
<220> FEATURE:
<223> OTHER INFORMATION: binding peptide

<400> SEQUENCE: 37

Thr Phe Val Gln Thr Pro Leu Ser His Leu Ile Ala
1               5                   10

<210> SEQ ID NO 38
<211> LENGTH: 12
<212> TYPE: PRT
<213> ORGANISM: Artificial
<220> FEATURE:
<223> OTHER INFORMATION: binding peptide

<400> SEQUENCE: 38

Arg Val Pro Pro Ser Lys Leu Thr Arg Pro Pro Phe
1               5                   10
```

```
<210> SEQ ID NO 39
<211> LENGTH: 12
<212> TYPE: PRT
<213> ORGANISM: Artificial
<220> FEATURE:
<223> OTHER INFORMATION: binding peptide

<400> SEQUENCE: 39

His Ser Ile Tyr Ser Val Thr Pro Ser Thr Ala Ser
1               5                   10

<210> SEQ ID NO 40
<211> LENGTH: 12
<212> TYPE: PRT
<213> ORGANISM: Artificial
<220> FEATURE:
<223> OTHER INFORMATION: binding peptide

<400> SEQUENCE: 40

Leu Asn Thr Gln Asn His Ala Pro Leu Pro Ser Ile
1               5                   10

<210> SEQ ID NO 41
<211> LENGTH: 32
<212> TYPE: PRT
<213> ORGANISM: Artificial
<220> FEATURE:
<223> OTHER INFORMATION: binding peptide

<400> SEQUENCE: 41

Lys Tyr Asp Ser Arg His Leu His Thr His Ser His Gly Gly Gly Ser
1               5                   10                  15

Gly Gly Gly Ser Pro Asn Arg Leu Gly Arg Arg Pro Val Arg Trp Glu
            20                  25                  30

<210> SEQ ID NO 42
<211> LENGTH: 32
<212> TYPE: PRT
<213> ORGANISM: Artificial
<220> FEATURE:
<223> OTHER INFORMATION: binding peptide

<400> SEQUENCE: 42

Trp Pro His Ala Trp Lys Val Trp Trp Pro Ala Ser Gly Gly Gly Ser
1               5                   10                  15

Gly Gly Gly Ser Asn Trp Trp Trp Pro Pro Tyr Ile Arg His Gln Pro
            20                  25                  30

<210> SEQ ID NO 43
<211> LENGTH: 46
<212> TYPE: DNA
<213> ORGANISM: Artificial
<220> FEATURE:
<223> OTHER INFORMATION: binding peptide

<400> SEQUENCE: 43
gatccaaata tgatagccgt catctgcata cccatagcca tgagct                46

<210> SEQ ID NO 44
<211> LENGTH: 38
<212> TYPE: DNA
<213> ORGANISM: Artificial
<220> FEATURE:
<223> OTHER INFORMATION: complementary to 43

<400> SEQUENCE: 44
```
catggctatg ggtatgcaga tgacggctat catatttg                                    38

<210> SEQ ID NO 45
<211> LENGTH: 46
<212> TYPE: DNA
<213> ORGANISM: Artificial
<220> FEATURE:
<223> OTHER INFORMATION: binding peptide

<400> SEQUENCE: 45
gatccccgaa ccgtctgggc cgtcgtccgg tgcgttggga agagct                           46

<210> SEQ ID NO 46
<211> LENGTH: 38
<212> TYPE: DNA
<213> ORGANISM: Artificial
<220> FEATURE:
<223> OTHER INFORMATION: complementary to 45

<400> SEQUENCE: 46
cttcccaacg caccggacga cggcccagac ggttcggg                                    38

<210> SEQ ID NO 47
<211> LENGTH: 46
<212> TYPE: DNA
<213> ORGANISM: Artificial
<220> FEATURE:
<223> OTHER INFORMATION: binding peptide

<400> SEQUENCE: 47
gatccaaatg ctgctattat gatcatagcc atgcgctgag cgagct                           46

<210> SEQ ID NO 48
<211> LENGTH: 38
<212> TYPE: DNA
<213> ORGANISM: Artificial
<220> FEATURE:
<223> OTHER INFORMATION: complementary to 47

<400> SEQUENCE: 48
cgctcagcgc atggctatga tcataatagc agcatttg                                    38

<210> SEQ ID NO 49
<211> LENGTH: 46
<212> TYPE: DNA
<213> ORGANISM: Artificial
<220> FEATURE:
<223> OTHER INFORMATION: binding peptide

<400> SEQUENCE: 49
gatccgaata tctgagcgcg attgtggcgg cccgtggcc ggagct                            46

<210> SEQ ID NO 50
<211> LENGTH: 38
<212> TYPE: DNA
<213> ORGANISM: Artificial
<220> FEATURE:
<223> OTHER INFORMATION: complementary to 49

<400> SEQUENCE: 50
ccggccacgg gcccgccaca atcgcgctca gatattcg                                    38

<210> SEQ ID NO 51
<211> LENGTH: 46
<212> TYPE: DNA
<213> ORGANISM: Artificial

```
<220> FEATURE:
<223> OTHER INFORMATION: binding peptide

<400> SEQUENCE: 51
gatccaaact gtggattctg gaaccgaccg tgaccccgac cgagct                    46

<210> SEQ ID NO 52
<211> LENGTH: 38
<212> TYPE: DNA
<213> ORGANISM: Artificial
<220> FEATURE:
<223> OTHER INFORMATION: complementary to 51

<400> SEQUENCE: 52
cggtcggggt cacggtcggt tccagaatcc acagtttg                             38

<210> SEQ ID NO 53
<211> LENGTH: 46
<212> TYPE: DNA
<213> ORGANISM: Artificial
<220> FEATURE:
<223> OTHER INFORMATION: binding peptide

<400> SEQUENCE: 53
gatcccagag caacctgaaa gtgattccga gctggtggtt tgagct                    46

<210> SEQ ID NO 54
<211> LENGTH: 38
<212> TYPE: DNA
<213> ORGANISM: Artificial
<220> FEATURE:
<223> OTHER INFORMATION: complementary to 53

<400> SEQUENCE: 54
caaaccacca gctcggaatc actttcaggt tgctctgg                             38

<210> SEQ ID NO 55
<211> LENGTH: 46
<212> TYPE: DNA
<213> ORGANISM: Artificial
<220> FEATURE:
<223> OTHER INFORMATION: binding peptide

<400> SEQUENCE: 55
gatcctggat tccgccgcag tggagccgtc tgattgaacc ggagct                    46

<210> SEQ ID NO 56
<211> LENGTH: 38
<212> TYPE: DNA
<213> ORGANISM: Artificial
<220> FEATURE:
<223> OTHER INFORMATION: complementary to 55

<400> SEQUENCE: 56
ccggttcaat cagacggctc cactgcggcg gaatccag                             38

<210> SEQ ID NO 57
<211> LENGTH: 46
<212> TYPE: DNA
<213> ORGANISM: Artificial
<220> FEATURE:
<223> OTHER INFORMATION: binding peptide

<400> SEQUENCE: 57
gatccgatca tccgcaggcg aaaccgaact ggtatggcgt ggagct                    46
```

<210> SEQ ID NO 58
<211> LENGTH: 38
<212> TYPE: DNA
<213> ORGANISM: Artificial
<220> FEATURE:
<223> OTHER INFORMATION: complementary to 57

<400> SEQUENCE: 58
ccacgccata ccagttcggt ttcgcctgcg gatgatcg                        38

<210> SEQ ID NO 59
<211> LENGTH: 46
<212> TYPE: DNA
<213> ORGANISM: Artificial
<220> FEATURE:
<223> OTHER INFORMATION: binding peptide

<400> SEQUENCE: 59
gatccggcct gccgccgtat agcccgcatc gtctggcgca ggagct              46

<210> SEQ ID NO 60
<211> LENGTH: 38
<212> TYPE: DNA
<213> ORGANISM: Artificial
<220> FEATURE:
<223> OTHER INFORMATION: complementary to 59

<400> SEQUENCE: 60
cctgcgccag acgatgcggg ctatacggcg gcaggccg                        38

<210> SEQ ID NO 61
<211> LENGTH: 46
<212> TYPE: DNA
<213> ORGANISM: Artificial
<220> FEATURE:
<223> OTHER INFORMATION: binding peptide

<400> SEQUENCE: 61
gatccaaact gaccacccag tatatggcgc gtagcagcag cgagct              46

<210> SEQ ID NO 62
<211> LENGTH: 38
<212> TYPE: DNA
<213> ORGANISM: Artificial
<220> FEATURE:
<223> OTHER INFORMATION: complementary to 61

<400> SEQUENCE: 62
cgctgctgct acgcgccata tactgggtgg tcagtttg                        38

<210> SEQ ID NO 63
<211> LENGTH: 46
<212> TYPE: DNA
<213> ORGANISM: Artificial
<220> FEATURE:
<223> OTHER INFORMATION: binding peptide

<400> SEQUENCE: 63
gatccaaagt gtggatgctg ccgccgctgc cgcaggcgac cgagct              46

<210> SEQ ID NO 64
<211> LENGTH: 38
<212> TYPE: DNA
<213> ORGANISM: Artificial
<220> FEATURE:
<223> OTHER INFORMATION: complementary to 63

<400> SEQUENCE: 64
cggtcgcctg cggcagcggc ggcagcatcc acactttg                                    38

<210> SEQ ID NO 65
<211> LENGTH: 46
<212> TYPE: DNA
<213> ORGANISM: Artificial
<220> FEATURE:
<223> OTHER INFORMATION: binding peptide

<400> SEQUENCE: 65
gatccaacgt gaccagcacc gcgtttattg atacccegtg ggagct                           46

<210> SEQ ID NO 66
<211> LENGTH: 38
<212> TYPE: DNA
<213> ORGANISM: Artificial
<220> FEATURE:
<223> OTHER INFORMATION: complementary to 65

<400> SEQUENCE: 66
cccacggggt atcaataaac gcggtgctgg tcacgttg                                    38

<210> SEQ ID NO 67
<211> LENGTH: 46
<212> TYPE: DNA
<213> ORGANISM: Artificial
<220> FEATURE:
<223> OTHER INFORMATION: binding peptide

<400> SEQUENCE: 67
gatcccgtct gaacctggat attattgcgg tgaccagcgt ggagct                           46

<210> SEQ ID NO 68
<211> LENGTH: 38
<212> TYPE: DNA
<213> ORGANISM: Artificial
<220> FEATURE:
<223> OTHER INFORMATION: complementary to 67

<400> SEQUENCE: 68
ccacgctggt caccgcaata atatccaggt tcagacgg                                    38

<210> SEQ ID NO 69
<211> LENGTH: 46
<212> TYPE: DNA
<213> ORGANISM: Artificial
<220> FEATURE:
<223> OTHER INFORMATION: binding peptide

<400> SEQUENCE: 69
gatccaccct gccgagcccg ctggcgctgc tgaccgtgca tgagct                           46

<210> SEQ ID NO 70
<211> LENGTH: 38
<212> TYPE: DNA
<213> ORGANISM: Artificial
<220> FEATURE:
<223> OTHER INFORMATION: complementary to 69

<400> SEQUENCE: 70
catgcacggt cagcagcgcc agcgggctcg gcagggtg                                    38

<210> SEQ ID NO 71

```
<211> LENGTH: 46
<212> TYPE: DNA
<213> ORGANISM: Artificial
<220> FEATURE:
<223> OTHER INFORMATION: binding peptide

<400> SEQUENCE: 71
gatccaccaa ccgtcataac ccgcatcatc tgcatcatgt ggagct        46

<210> SEQ ID NO 72
<211> LENGTH: 38
<212> TYPE: DNA
<213> ORGANISM: Artificial
<220> FEATURE:
<223> OTHER INFORMATION: complementary to 71

<400> SEQUENCE: 72
ccacatgatg cagatgatgc gggttatgac ggttggtg               38

<210> SEQ ID NO 73
<211> LENGTH: 46
<212> TYPE: DNA
<213> ORGANISM: Artificial
<220> FEATURE:
<223> OTHER INFORMATION: binding peptide

<400> SEQUENCE: 73
gatcctggcc gcatgcgtgg aaagtgtggt ggccggcgag cgagct        46

<210> SEQ ID NO 74
<211> LENGTH: 38
<212> TYPE: DNA
<213> ORGANISM: Artificial
<220> FEATURE:
<223> OTHER INFORMATION: complementary to 73

<400> SEQUENCE: 74
cgctcgccgg ccaccacact ttccacgcat gcggccag               38

<210> SEQ ID NO 75
<211> LENGTH: 46
<212> TYPE: DNA
<213> ORGANISM: Artificial
<220> FEATURE:
<223> OTHER INFORMATION: binding peptide

<400> SEQUENCE: 75
gatccaactg gtggtggccg ccgtatattc gtcatcagcc ggagct        46

<210> SEQ ID NO 76
<211> LENGTH: 38
<212> TYPE: DNA
<213> ORGANISM: Artificial
<220> FEATURE:
<223> OTHER INFORMATION: complementary to 75

<400> SEQUENCE: 76
ccggctgatg acgaatatac ggcggccacc accagttg               38

<210> SEQ ID NO 77
<211> LENGTH: 46
<212> TYPE: DNA
<213> ORGANISM: Artificial
<220> FEATURE:
<223> OTHER INFORMATION: binding peptide

<400> SEQUENCE: 77
```

```
gatcctggca ttggagctgg accccgtggc cgagccatca tgagct                    46

<210> SEQ ID NO 78
<211> LENGTH: 38
<212> TYPE: DNA
<213> ORGANISM: Artificial
<220> FEATURE:
<223> OTHER INFORMATION: complementary to 77

<400> SEQUENCE: 78
catgatggct cggccacggg gtccagctcc aatgccag                              38

<210> SEQ ID NO 79
<211> LENGTH: 46
<212> TYPE: DNA
<213> ORGANISM: Artificial
<220> FEATURE:
<223> OTHER INFORMATION: binding peptide

<400> SEQUENCE: 79
gatcctggcc gtgggcgtgg catccgagcc gtgatgtgta tgagct                    46

<210> SEQ ID NO 80
<211> LENGTH: 38
<212> TYPE: DNA
<213> ORGANISM: Artificial
<220> FEATURE:
<223> OTHER INFORMATION: complementary to 79

<400> SEQUENCE: 80
catacacatc acggctcgga tgccacgccc acggccag                              38

<210> SEQ ID NO 81
<211> LENGTH: 46
<212> TYPE: DNA
<213> ORGANISM: Artificial
<220> FEATURE:
<223> OTHER INFORMATION: binding peptide

<400> SEQUENCE: 81
gatcctggca tggctattgg tatagcaacc tgaacaccac cgagct                    46

<210> SEQ ID NO 82
<211> LENGTH: 38
<212> TYPE: DNA
<213> ORGANISM: Artificial
<220> FEATURE:
<223> OTHER INFORMATION: complementary to 81

<400> SEQUENCE: 82
cggtggtgtt caggttgcta taccaatagc catgccag                              38

<210> SEQ ID NO 83
<211> LENGTH: 46
<212> TYPE: DNA
<213> ORGANISM: Artificial
<220> FEATURE:
<223> OTHER INFORMATION: binding peptide

<400> SEQUENCE: 83
gatcctggtg gaccccgtgg atgagccatg cgtatccggt ggagct                    46

<210> SEQ ID NO 84
<211> LENGTH: 38
<212> TYPE: DNA
```

<210> SEQ ID NO 85
<211> LENGTH: 46
<212> TYPE: DNA
<213> ORGANISM: Artificial
<220> FEATURE:
<223> OTHER INFORMATION: complementary to 83

<400> SEQUENCE: 84
ccaccggata cgcatggctc atccacgggg tccaccag        38

<210> SEQ ID NO 85
<211> LENGTH: 46
<212> TYPE: DNA
<213> ORGANISM: Artificial
<220> FEATURE:
<223> OTHER INFORMATION: binding peptide

<400> SEQUENCE: 85
gatcctggcc gaacccgtat tggggctggt ttgcggcggt ggagct        46

<210> SEQ ID NO 86
<211> LENGTH: 38
<212> TYPE: DNA
<213> ORGANISM: Artificial
<220> FEATURE:
<223> OTHER INFORMATION: complementary to 85

<400> SEQUENCE: 86
ccaccgccgc aaaccagccc caatacgggt tcggccag        38

<210> SEQ ID NO 87
<211> LENGTH: 46
<212> TYPE: DNA
<213> ORGANISM: Artificial
<220> FEATURE:
<223> OTHER INFORMATION: binding peptide

<400> SEQUENCE: 87
gatccaccag ctggcatacc tggtggtggc gtcagccgcc ggagct        46

<210> SEQ ID NO 88
<211> LENGTH: 38
<212> TYPE: DNA
<213> ORGANISM: Artificial
<220> FEATURE:
<223> OTHER INFORMATION: 87

<400> SEQUENCE: 88
ccggcggctg acgccaccac caggtatgcc agctggtg        38

<210> SEQ ID NO 89
<211> LENGTH: 46
<212> TYPE: DNA
<213> ORGANISM: Artificial
<220> FEATURE:
<223> OTHER INFORMATION: binding peptide

<400> SEQUENCE: 89
gatccaacgc gtggcataaa tattggtggc cgattaccaa agagct        46

<210> SEQ ID NO 90
<211> LENGTH: 38
<212> TYPE: DNA
<213> ORGANISM: Artificial
<220> FEATURE:
<223> OTHER INFORMATION: complementary to 89

<400> SEQUENCE: 90
ctttggtaat cggccaccaa tatttatgcc acgcgttg        38

<210> SEQ ID NO 91
<211> LENGTH: 46
<212> TYPE: DNA
<213> ORGANISM: Artificial
<220> FEATURE:
<223> OTHER INFORMATION: binding peptide

<400> SEQUENCE: 91
gatcccatcc gaacaacgat tggagcaaag cgccgcagtt tgagct         46

<210> SEQ ID NO 92
<211> LENGTH: 38
<212> TYPE: DNA
<213> ORGANISM: Artificial
<220> FEATURE:
<223> OTHER INFORMATION: complementary to 91

<400> SEQUENCE: 92
caaactgcgg cgctttgctc caatcgttgt tcggatgg             38

<210> SEQ ID NO 93
<211> LENGTH: 46
<212> TYPE: DNA
<213> ORGANISM: Artificial
<220> FEATURE:
<223> OTHER INFORMATION: binding peptide

<400> SEQUENCE: 93
gatcctggtg accccgcag ccgtggtgga gctttccgat tgagct         46

<210> SEQ ID NO 94
<211> LENGTH: 38
<212> TYPE: DNA
<213> ORGANISM: Artificial
<220> FEATURE:
<223> OTHER INFORMATION: complementary to 93

<400> SEQUENCE: 94
caatcggaaa gctccaccac ggctgcgggg tccaccag             38

<210> SEQ ID NO 95
<211> LENGTH: 46
<212> TYPE: DNA
<213> ORGANISM: Artificial
<220> FEATURE:
<223> OTHER INFORMATION: binding peptide

<400> SEQUENCE: 95
gatcctggcc gcataccagc tgtggcaga ccccgctgac cgagct         46

<210> SEQ ID NO 96
<211> LENGTH: 38
<212> TYPE: DNA
<213> ORGANISM: Artificial
<220> FEATURE:
<223> OTHER INFORMATION: 95

<400> SEQUENCE: 96
cggtcagcgg ggtctgccac cagctggtat gcggccag             38

<210> SEQ ID NO 97
<211> LENGTH: 46
<212> TYPE: DNA
<213> ORGANISM: Artificial
<220> FEATURE:

<223> OTHER INFORMATION: binding peptide

<400> SEQUENCE: 97
gatcctggca tgtgaactgg gatccgatgg cgtggtatcg tgagct    46

<210> SEQ ID NO 98
<211> LENGTH: 38
<212> TYPE: DNA
<213> ORGANISM: Artificial
<220> FEATURE:
<223> OTHER INFORMATION: complementary to 97

<400> SEQUENCE: 98
cacgatacca cgccatcgga tcccagttca catgccag    38

<210> SEQ ID NO 99
<211> LENGTH: 46
<212> TYPE: DNA
<213> ORGANISM: Artificial
<220> FEATURE:
<223> OTHER INFORMATION: binding peptide

<400> SEQUENCE: 99
gatccagctg gccgtggtgg accgcgtatc gtgtgcatag cgagct    46

<210> SEQ ID NO 100
<211> LENGTH: 38
<212> TYPE: DNA
<213> ORGANISM: Artificial
<220> FEATURE:
<223> OTHER INFORMATION: complementary to 99

<400> SEQUENCE: 100
cgctatgcac acgatacgcg gtccaccacg gccagctg    38

<210> SEQ ID NO 101
<211> LENGTH: 46
<212> TYPE: DNA
<213> ORGANISM: Artificial
<220> FEATURE:
<223> OTHER INFORMATION: binding peptide

<400> SEQUENCE: 101
gatcctggca tagcaactgg tatcagagca ttccgcaggt ggagct    46

<210> SEQ ID NO 102
<211> LENGTH: 38
<212> TYPE: DNA
<213> ORGANISM: Artificial
<220> FEATURE:
<223> OTHER INFORMATION: complementary to 101

<400> SEQUENCE: 102
ccacctgcgg aatgctctga taccagttgc tatgccag    38

<210> SEQ ID NO 103
<211> LENGTH: 46
<212> TYPE: DNA
<213> ORGANISM: Artificial
<220> FEATURE:
<223> OTHER INFORMATION: binding peptide

<400> SEQUENCE: 103
gatccggcta ttggccgtgg aaatttgaac atgcgaccgt ggagct    46

```
<210> SEQ ID NO 104
<211> LENGTH: 38
<212> TYPE: DNA
<213> ORGANISM: Artificial
<220> FEATURE:
<223> OTHER INFORMATION: complementary to 103

<400> SEQUENCE: 104
ccacggtcgc atgttcaaat ttccacggcc aatagccg                          38

<210> SEQ ID NO 105
<211> LENGTH: 46
<212> TYPE: DNA
<213> ORGANISM: Artificial
<220> FEATURE:
<223> OTHER INFORMATION: binding peptide

<400> SEQUENCE: 105
gatccgcgtg gtggccgacc acctttccgc cgtattatta tgagct                 46

<210> SEQ ID NO 106
<211> LENGTH: 38
<212> TYPE: DNA
<213> ORGANISM: Artificial
<220> FEATURE:
<223> OTHER INFORMATION: complementary to 105

<400> SEQUENCE: 106
cataataata cggcggaaag gtggtcggcc accacgcg                          38

<210> SEQ ID NO 107
<211> LENGTH: 46
<212> TYPE: DNA
<213> ORGANISM: Artificial
<220> FEATURE:
<223> OTHER INFORMATION: binding peptide

<400> SEQUENCE: 107
gatccaaccc gtggtggagc cattattatc cgcgtagcgt ggagct                 46

<210> SEQ ID NO 108
<211> LENGTH: 38
<212> TYPE: DNA
<213> ORGANISM: Artificial
<220> FEATURE:
<223> OTHER INFORMATION: complementary to 107

<400> SEQUENCE: 108
ccacgctacg cggataataa tggctccacc acgggttg                          38

<210> SEQ ID NO 109
<211> LENGTH: 46
<212> TYPE: DNA
<213> ORGANISM: Artificial
<220> FEATURE:
<223> OTHER INFORMATION: binding peptide

<400> SEQUENCE: 109
gatcctggcc gcataactat ccgctgaacc atagcaaccc ggagct                 46

<210> SEQ ID NO 110
<211> LENGTH: 38
<212> TYPE: DNA
<213> ORGANISM: Artificial
<220> FEATURE:
<223> OTHER INFORMATION: complementary to 109
```

```
<400> SEQUENCE: 110
ccgggttgct atggttcagc ggatagttat gcggccag                              38

<210> SEQ ID NO 111
<211> LENGTH: 46
<212> TYPE: DNA
<213> ORGANISM: Artificial
<220> FEATURE:
<223> OTHER INFORMATION: binding peptide

<400> SEQUENCE: 111
gatccacctg ggcgcatccg ctggaaagcg attatctgcg tgagct                     46

<210> SEQ ID NO 112
<211> LENGTH: 38
<212> TYPE: DNA
<213> ORGANISM: Artificial
<220> FEATURE:
<223> OTHER INFORMATION: complementary to 111

<400> SEQUENCE: 112
cacgcagata atcgctttcc agcggatgcg cccaggtg                              38

<210> SEQ ID NO 113
<211> LENGTH: 46
<212> TYPE: DNA
<213> ORGANISM: Artificial
<220> FEATURE:
<223> OTHER INFORMATION: binding peptide

<400> SEQUENCE: 113
gatcccatac ctattatcat gatggctggc gtctggcgcc ggagct                     46

<210> SEQ ID NO 114
<211> LENGTH: 38
<212> TYPE: DNA
<213> ORGANISM: Artificial
<220> FEATURE:
<223> OTHER INFORMATION: complementary to 113

<400> SEQUENCE: 114
ccggcgccag acgccagcca tcatgataat aggtatgg                              38

<210> SEQ ID NO 115
<211> LENGTH: 46
<212> TYPE: DNA
<213> ORGANISM: Artificial
<220> FEATURE:
<223> OTHER INFORMATION: binding peptide

<400> SEQUENCE: 115
gatccacctt tgtgcagacc ccgctgagcc atctgattgc ggagct                     46

<210> SEQ ID NO 116
<211> LENGTH: 38
<212> TYPE: DNA
<213> ORGANISM: Artificial
<220> FEATURE:
<223> OTHER INFORMATION: complementary to 115

<400> SEQUENCE: 116
ccgcaatcag atggctcagc ggggtctgca caaaggtg                              38

<210> SEQ ID NO 117
<211> LENGTH: 46
```

```
<212> TYPE: DNA
<213> ORGANISM: Artificial
<220> FEATURE:
<223> OTHER INFORMATION: binding peptide

<400> SEQUENCE: 117
gatcccgtgt gccgccgagc aaactgaccc gtccgccgtt tgagct            46

<210> SEQ ID NO 118
<211> LENGTH: 38
<212> TYPE: DNA
<213> ORGANISM: Artificial
<220> FEATURE:
<223> OTHER INFORMATION: complementary to 117

<400> SEQUENCE: 118
caaacggcgg acgggtcagt ttgctcggcg gcacacgg                     38

<210> SEQ ID NO 119
<211> LENGTH: 46
<212> TYPE: DNA
<213> ORGANISM: Artificial
<220> FEATURE:
<223> OTHER INFORMATION: binding peptide

<400> SEQUENCE: 119
gatcccatag catttatagc gtgaccccga gcaccgcgag cgagct            46

<210> SEQ ID NO 120
<211> LENGTH: 38
<212> TYPE: DNA
<213> ORGANISM: Artificial
<220> FEATURE:
<223> OTHER INFORMATION: complementary to 119

<400> SEQUENCE: 120
cgctcgcggt gctcggggtc acgctataaa tgctatgg                     38

<210> SEQ ID NO 121
<211> LENGTH: 46
<212> TYPE: DNA
<213> ORGANISM: Artificial
<220> FEATURE:
<223> OTHER INFORMATION: binding peptide

<400> SEQUENCE: 121
gatccctgaa cacccagaac catgcgccgc tgccgagcat tgagct            46

<210> SEQ ID NO 122
<211> LENGTH: 38
<212> TYPE: DNA
<213> ORGANISM: Artificial
<220> FEATURE:
<223> OTHER INFORMATION: complementary to 121

<400> SEQUENCE: 122
caatgctcgg cagcggcgca tggttctggg tgttcagg                     38

<210> SEQ ID NO 123
<211> LENGTH: 106
<212> TYPE: DNA
<213> ORGANISM: Artificial
<220> FEATURE:
<223> OTHER INFORMATION: binding peptide

<400> SEQUENCE: 123
```

```
gatccaaata tgatagccgt catctgcata cccatagcca tggcggcggc agcggcggcg    60
gcagcccgaa ccgtctgggc cgtcgtccgg tgcgttggga agagct                  106
```

<210> SEQ ID NO 124
<211> LENGTH: 98
<212> TYPE: DNA
<213> ORGANISM: Artificial
<220> FEATURE:
<223> OTHER INFORMATION: complementary to 123

<400> SEQUENCE: 124

```
cttcccaacg caccggacga cggcccagac ggttcgggct gccgccgccg ctgccgccgc    60
catggctatg ggtatgcaga tgacggctat catatttg                            98
```

<210> SEQ ID NO 125
<211> LENGTH: 106
<212> TYPE: DNA
<213> ORGANISM: Artificial
<220> FEATURE:
<223> OTHER INFORMATION: binding peptide

<400> SEQUENCE: 125

```
gatcctggcc gcatgcgtgg aaagtgtggt ggccggcgag cggcggcggc agcggcggcg    60
gcagcaactg gtggtggccg ccgtatattc gtcatcagcc ggagct                  106
```

<210> SEQ ID NO 126
<211> LENGTH: 98
<212> TYPE: DNA
<213> ORGANISM: Artificial
<220> FEATURE:
<223> OTHER INFORMATION: complementary to 125

<400> SEQUENCE: 126

```
ccggctgatg acgaatatac ggcggccacc accagttgct gccgccgccg ctgccgccgc    60
cgctcgccgg ccaccacact ttccacgcat gcggccag                            98
```

<210> SEQ ID NO 127
<211> LENGTH: 30
<212> TYPE: DNA
<213> ORGANISM: Artificial
<220> FEATURE:
<223> OTHER INFORMATION: 5' primer for NS4

<400> SEQUENCE: 127

```
ttcacaggat ccactgagct cgatgcccac                                     30
```

<210> SEQ ID NO 128
<211> LENGTH: 30
<212> TYPE: DNA
<213> ORGANISM: artificial
<220> FEATURE:
<223> OTHER INFORMATION: 3'primer for NS4

<400> SEQUENCE: 128

```
gatctgggct cgagccgact agtagtcgct                                     30
```

<210> SEQ ID NO 129
<211> LENGTH: 7
<212> TYPE: PRT
<213> ORGANISM: artificial
<220> FEATURE:
<223> OTHER INFORMATION: spacer

<400> SEQUENCE: 129

```
-continued

Gly Gly Gly Ser Gly Gly Ser
1               5
```